United States Patent
Tan et al.

(10) Patent No.: US 11,453,902 B2
(45) Date of Patent: Sep. 27, 2022

(54) VERSATILE, HIGH-YIELD PROTEIN PRODUCTION EX VIVO

(71) Applicant: The Regents of the University of California, Oakland, CA (US)

(72) Inventors: Cheemeng Tan, Davis, CA (US); Luis Eduardo Contreras Llano, Davis, CA (US); Conary Meyer, Davis, CA (US); Fernando Villarreal, Davis, CA (US)

(73) Assignee: The Regents of the University of California, Oakland, CA (US)

( * ) Notice: Subject to any disclaimer, the term of this patent is extended or adjusted under 35 U.S.C. 154(b) by 0 days.

(21) Appl. No.: 16/914,997

(22) Filed: Jun. 29, 2020

(65) Prior Publication Data

US 2020/0407765 A1 Dec. 31, 2020

Related U.S. Application Data

(60) Provisional application No. 62/868,790, filed on Jun. 28, 2019.

(51) Int. Cl.
*C12P 21/02* (2006.01)
*C12N 15/67* (2006.01)
*C07K 14/47* (2006.01)

(52) U.S. Cl.
CPC .......... *C12P 21/02* (2013.01); *C07K 14/4702* (2013.01); *C12N 15/67* (2013.01)

(58) Field of Classification Search
None
See application file for complete search history.

(56) References Cited

U.S. PATENT DOCUMENTS

2019/0376069 A1 12/2019 Villarreal et al.

FOREIGN PATENT DOCUMENTS

WO 2018/148215 A1 2/2018

OTHER PUBLICATIONS

Yoshihiro Shimizu et al Cell-free translation reconstituted with purified components. Aug. 2001, vol. 19, nature biotechnology p. 715-755. (Year: 2001).*
Liu, Y et al.; "Versatile, High-yield Protein Production ex vivo"; Slide Presentation; Apr. 25, 2019; 51 pages.
"Technical Bulletin: *E. coli* S30 Extract System for Linear Templates"; Promega Corporation; Madison, WI; Jun. 2015; 21 pages.
Contreras-Llano, L.E. et al.; "Holistic engineering of cell-free systems through proteome-reprogramming synthetic circuits"; *Nature Communications*; vol. 11 2020; 10 pages.
Villarreal, F. et al.; "Synthetic microbial consortia enable rapid assembly of pure translation machinery"; *Nature Chemical Biology*: vol. 14; Jan. 2018; 13 pages.

* cited by examiner

*Primary Examiner* — Kagnew H Gebreyesus
(74) *Attorney, Agent, or Firm* — Kilpatrick Townsend and Stockton LLP

(57) ABSTRACT

A cell lysate or cell-free protein synthesis system comprising recombinant translational proteins and uses thereof are provided.

12 Claims, 11 Drawing Sheets

VERSATILE, HIGH-YIELD PROTEIN PRODUCTION EX VIVO

CROSS-REFERENCES TO RELATED APPLICATIONS

The present patent application claims benefit of priority to U.S. Provisional Patent Application No. 62/868,790, filed Jun. 28, 2019, which is incorporated by reference for all purposes.

BACKGROUND OF THE INVENTION

The mantra of synthetic biology advocates for the use of orthogonal genetic modules to engineer and control cellular behavior [Brophy, J. A. N. & Voigt, C. A., Nat. Methods 11, 508-520 (2014)]. However, the use of orthogonal genetic modules often faces the challenges of varying cellular context, such as growth rate, crosstalk, and noise [Cardinale, S. & Arkin, A. P., Biotechnol. J. 7, 856-866 (2012)]. These challenges highlight the necessity to complement orthogonal genetic module design with a system-based approach that functions in conjunction with cell physiology [Purnick, P. E. M. & Weiss, R., Nature Reviews Molecular Cell Biology 10, 410-422 (2009)]. Such systems-synthetic biology approaches have been applied in two major ways. First, systems-level properties can be considered for the control of local synthetic modules. For instance, previous studies have investigated the impact of global physiology on cell-free protein synthesis [Bosdriesz, E. et al., FEBS J. 282, 2029-2044 (2015)]. Second, the global host circuits are modified before the insertion of local synthetic modules. One classic example is the gene knock-out and knock-in of the BL21 E. coli strain for subsequent conversion into BL21 (DE3) using lacUV5-T7 RNAP-based synthetic modules [Studier, F. W. & Moffatt, B. A., J. Mol. Biol. 189, 113-130 (1986)]. A powerful alternative, referred to as the holistic synthetic biology approach in this work, is to use local synthetic modules to reprogram the global host physiology, which in turn becomes beneficial to the function of the local synthetic modules.

BRIEF SUMMARY OF THE INVENTION

The present application provides for a cell lysate (e.g., cell-free) from a cell mixture that heterologously expresses 2, 3, 4, 5, 6, 7, 8, 9, 10, 11 or all of the following polypeptides: translational initiation factor 1 (IF1); translational initiation factor 2 (IF2); translational initiation factor 3 (IF3); translational elongation factor G (EF-G); translational elongation factor Tu (EF-Tu); translational elongation factor Ts (EF-Ts); translational elongation factor 4 (EF4); translational release factor 1 (RF1), translational release factor 2 (RF2) (which can optionally be omitted), translational release factor 3 (RF3); ribosome recycling factor (RRF); and (optionally) Ala-tRNA transferase. In some embodiments, the polypeptides further comprise one or more or all of: Val-tRNA transferase; Met-tRNA transferase; Ile-tRNA transferase; Thr-tRNA transferase; Lys-tRNA transferase; Glu-tRNA transferase, Asp-tRNA transferase; Asn-tRNA transferase; Leu-tRNA transferase; Arg-tRNA transferase; Cys-tRNA transferase; Trp-tRNA transferase; Phe-tRNA transferase B; Pro-tRNA transferase; Ser-tRNA transferase; Phe-tRNA transferase A; Gln-tRNA transferase; Tyr-tRNA transferase; Met-tRNA formyltransferase; Gly-tRNA transferase B; His-tRNA transferase; and Gly-tRNA transferase A.

In some embodiments, the cell mixture comprises a plurality of different cells, wherein different cells heterologously express one or more of the polypeptides such that the cell mixture expresses each of the polypeptides.

In some embodiments, the cell mixture comprises seven different cells heterologously expressing different of the polypeptides. In some embodiments, the cell mixture comprises the following cells: a first cell heterologously expressing EF-Tu and EF-Ts; a second cell heterologously expressing IF1 and IF2; a third cell heterologously expressing EF-G and IF3; a fourth cell heterologously expressing Ala-tRNA transferase and EF4; a fifth cell heterologously expressing RF1 and RF2; a sixth cell heterologously expressing RF3 and RRF; a seventh cell heterologously expressing EF-G.

In some embodiments, wherein the cell lysate further comprises an exogenous nuclease inhibitor. In some embodiments, the exogenous nuclease inhibitor is Gam. In some embodiments, the nuclease inhibitor is expressed from a cell in the cell mixture.

In some embodiments, expression of one or more of polypeptides is encoded by a polynucleotide operably linked to an exogenous promoter. In some embodiments, the exogenous promoter is a T7 promoter.

Also provided are methods of forming a cell-free cell lysate that comprises elevated levels of proteins that promote translation. In some embodiments, the method comprises providing plurality of different cells, wherein different cells heterologously express one or more of the polypeptides such that the cell mixture expresses 2, 3, 4, 5, 6, 7, 8, 9, 10, 11 or all of the following polypeptides: translational initiation factor 1 (IF1); translational initiation factor 2 (IF2) (which can optionally be omitted); translational initiation factor 3 (IF3); translational elongation factor G (EF-G); translational elongation factor Tu (EF-Tu); translational elongation factor Ts (EF-Ts); translational elongation factor 4 (EF4); translational release factor 1 (RF1), translational release factor 2 (RF2), translational release factor 3 (RF3); ribosome recycling factor (RRF); and optionally Ala-tRNA transferase; and lysing the cells, thereby producing a cell-free cell lysate.

In some embodiments, the different cells are in a cell mixture and the lysing comprises lysing cells in the cell mixture. In some embodiments, the different cells are lysed separately and the resulting cell lysates are combined to form the cell-free cell lysate.

Also provided is a method of performing cell-free protein translation. In some embodiments, the method comprises contacting an RNA comprising a protein coding sequence to the cell lysate as described above or elsewhere herein; and incubating the cell lysate under conditions to allow for translation of the protein coding sequence into a translated protein. In some embodiments, further comprising purifying the translated protein from the cell lysate.

1A) Graphical representation of the production of BL-7$S_{WCE}$ showing the overexpression of 11 Translation Factors and their influence in different stages of translation.

1B) BL-7$S_{WCE}$ exhibits a higher yield than conventional cell lysates in batch CFPS reactions. We expressed deGFP encoded in the plasmid pIVEX-Eps-deGFP (10 μg μL$^{-1}$) using BL-7$S_{WCE}$, BL-E$_{WCE}$, BL-P$_{WCE}$, and the commercial S30 System. Reaction assembly, incubation conditions, and deGFP quantification are described in Methods, Sections M3

& M4. Reactions assembled using BL-7S$_{WCE}$ exhibit deGFP expression ~2 to ~3-fold higher than the controls. Data are presented as mean values & error bars represent s.d. (n=3 independent experiments). Standard two-tail t-test.

1C) BL-7S$_{WCE}$ exhibit ~2-fold more deGFP expression than the controls in semi-continuous exchange reactions. Assembly of the reactions and deGFP quantification are described in Methods, Sections M4 & M5. Data are presented as mean values & error bars represent s.d. (n=3 independent experiments). Standard two-tail t-test.

1D) Time series showing the expression dynamics of BL-7S$_{WCE}$ compared to controls under semi-continuous agitation. Reaction assembly, incubation conditions, and deGFP quantification are described in Methods, Sections M3 & M4. Data are presented as mean values & error bars represent 95% Confidence Interval (n=4 independent experiments).

Figure 1A:
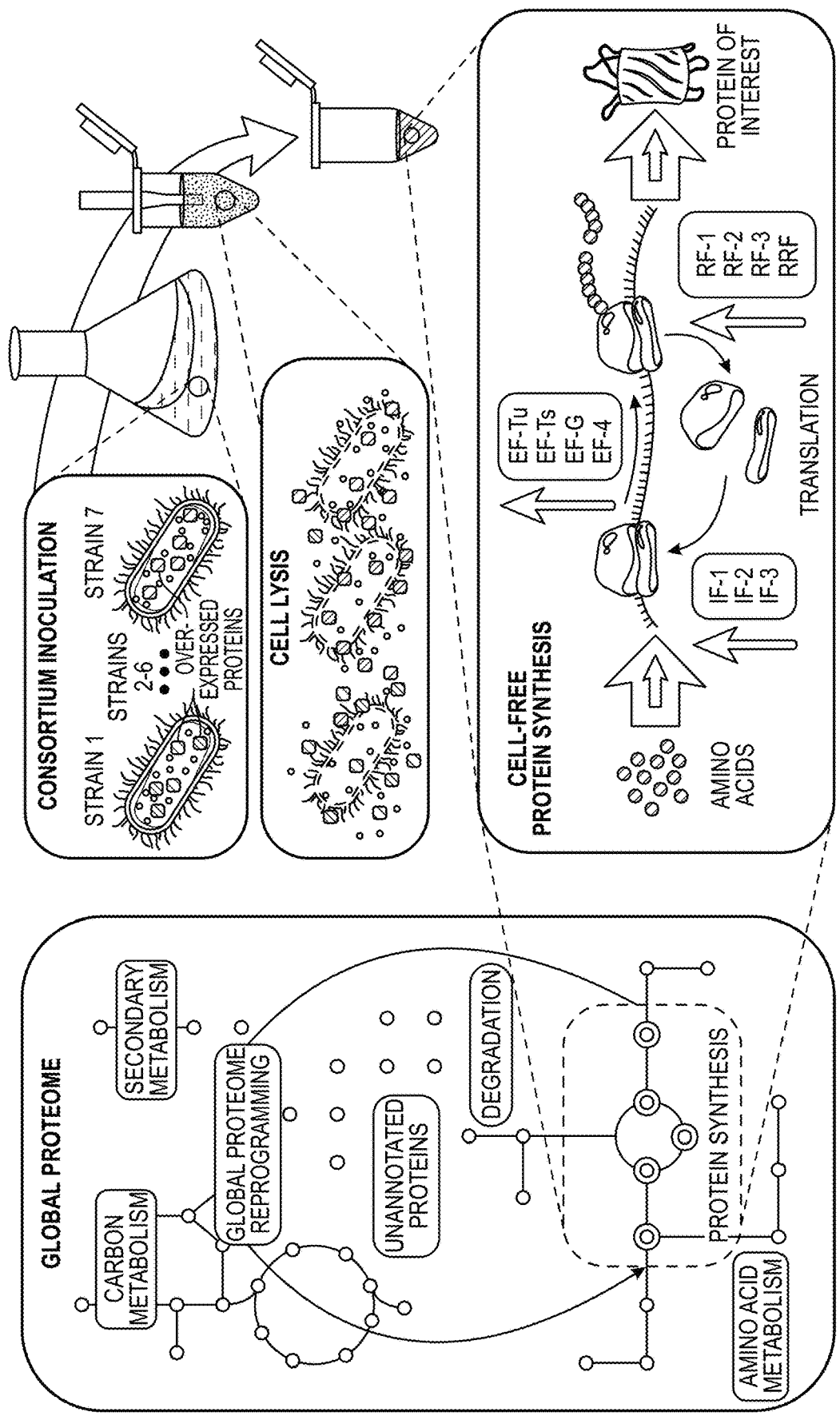
FIGS. 1A-D: A holistic synthetic-biology approach to enhance cell-free systems.
Figure 1C:
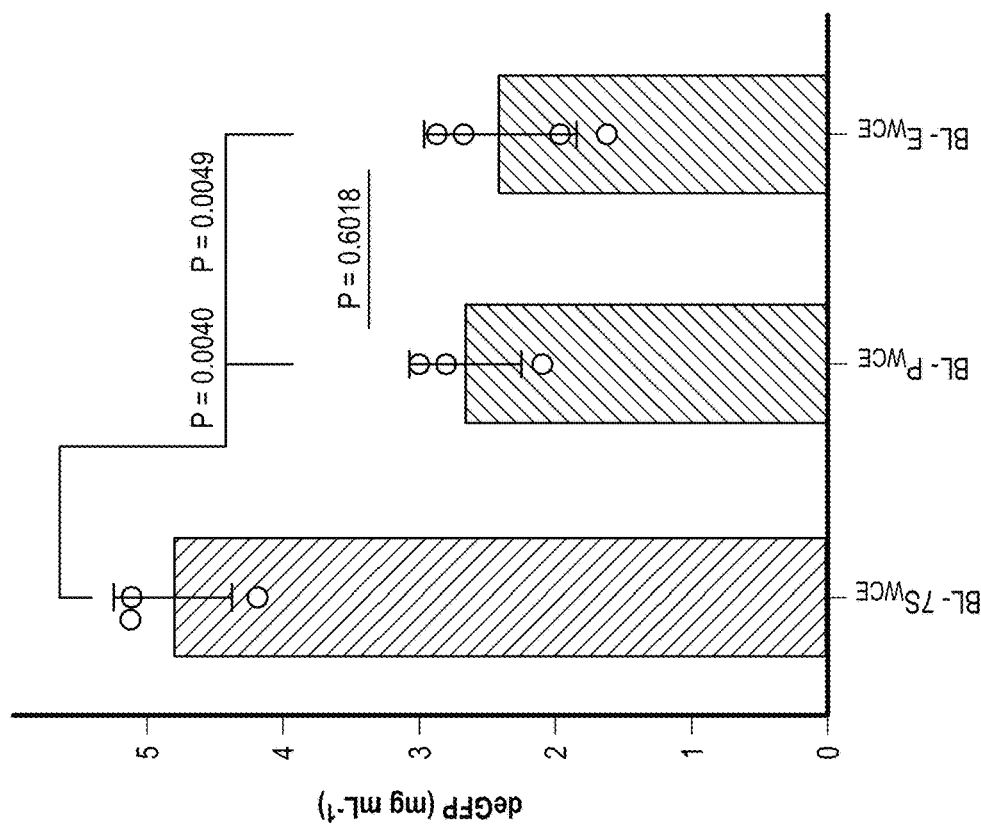
Figure 1B:
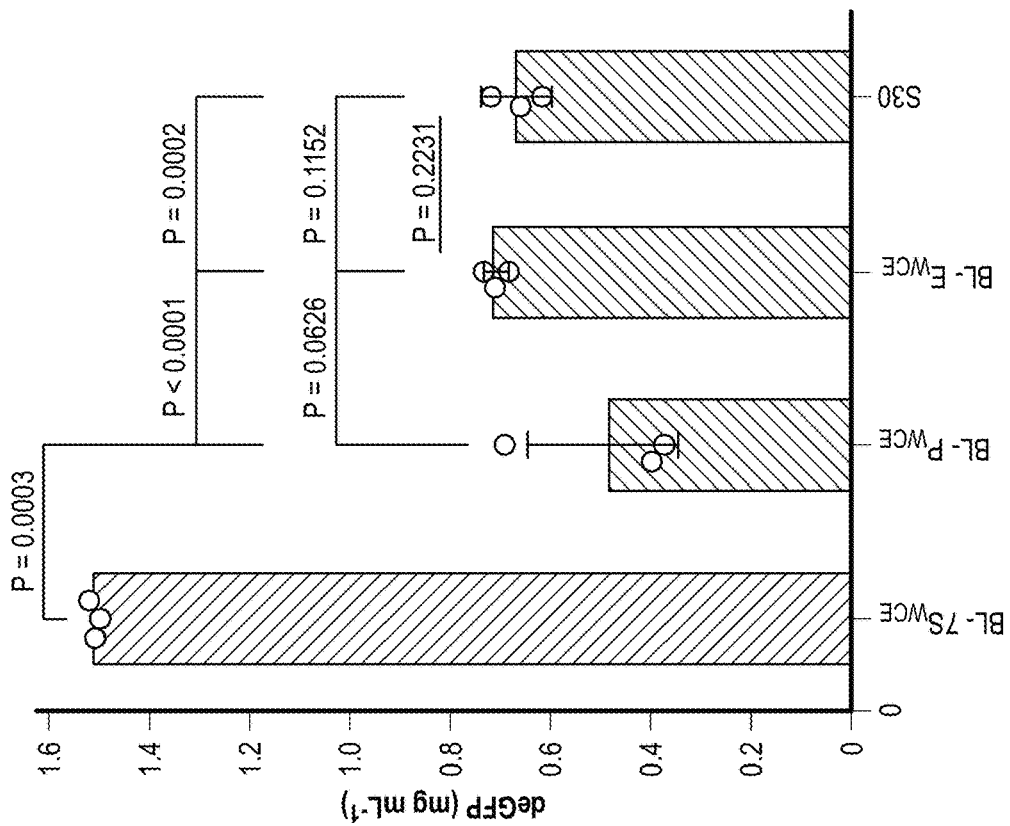
Figure 1D:
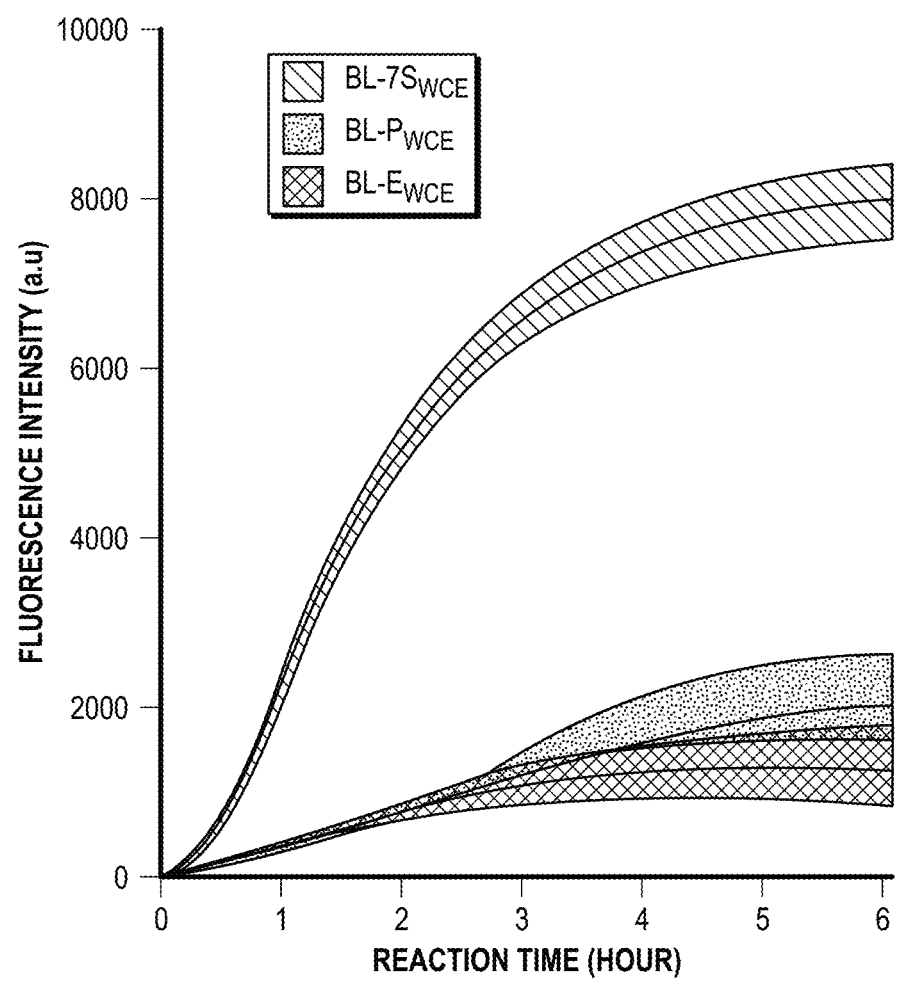

Source data for FIGS. 1B-D are provided as a Source Data file.

Figure 2A:
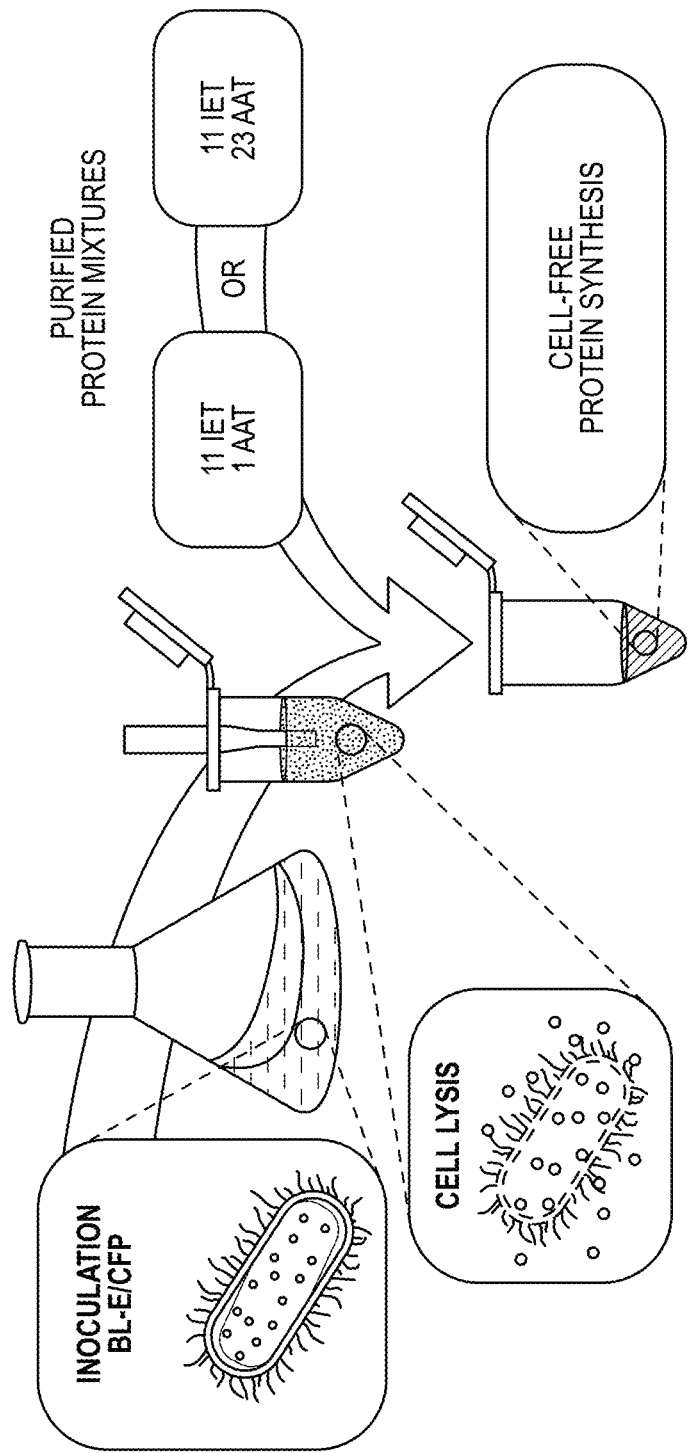
Figure 2B:
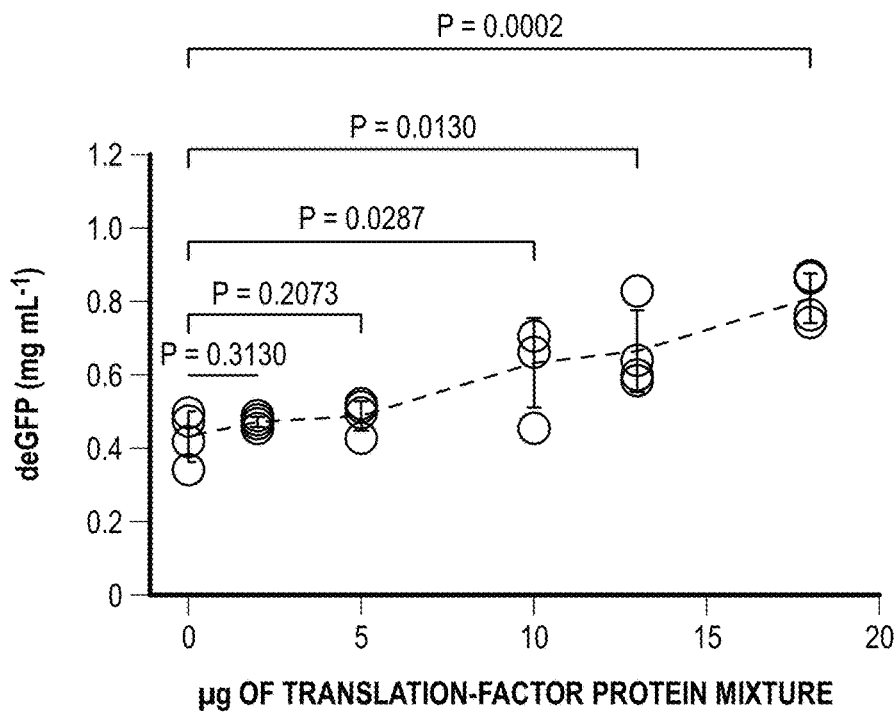
Figure 2C:
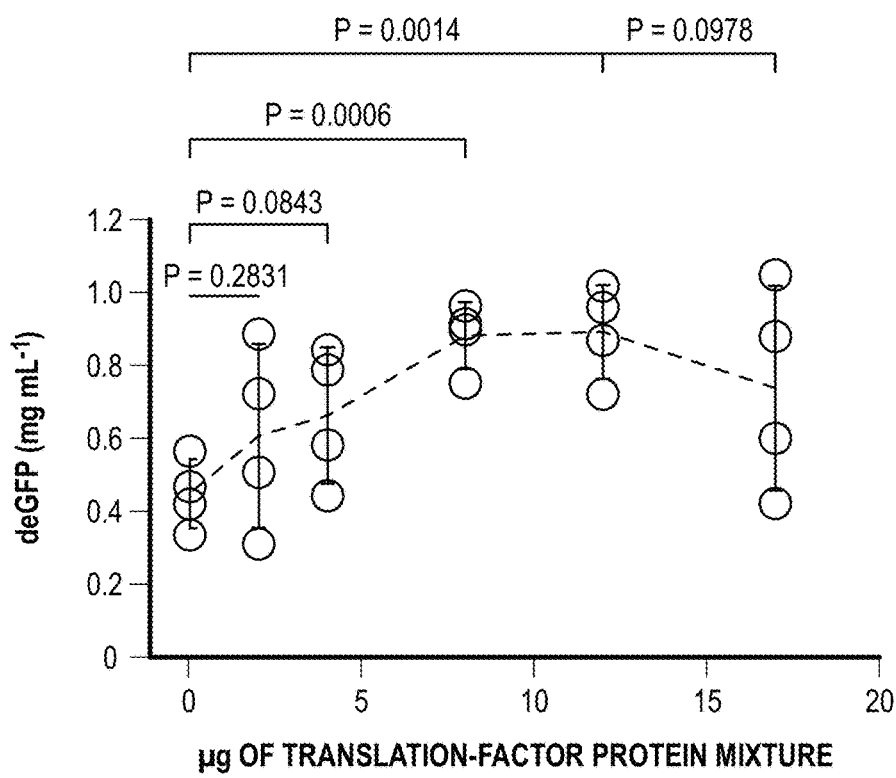

FIGS. 2A-C: Supplemented translation machinery partially enhances protein expression.

2A) Graphical representation of the supplementation of purified translation factors to CFPS reactions assembled using BL-E$_{WCE}$ & BL-CFP$_{WCE}$. Two different mixtures of purified translation machinery were produced, one with 11 IET (Initiation, Elongation, Termination factors) and 1 AAT (Aminoacyl-tRNA Transferases) and the other with 11 IET and 23 AAT proteins.

2B) Expression yield of BL-E$_{WCE}$ increases proportionally with the supplementation of purified translation machinery. The addition of 10 and 13 μg of purified translation factors to a 10 μL CFPS reaction increases protein yield by ~1.5-fold. Supplementation of up to 18 μg of purified translation factors increases protein yield by ~2-fold. Reaction assembly, purified protein supplementation, and incubation conditions are described in Methods, Sections M3&M6. Data are presented as mean values & error bars represent s.d. (n=4 independent experiments). Standard two-tail t-test.

2C) Expression yield of BL-CFP$_{WCE}$ increases proportionally with the supplementation of purified translation machinery. The addition of 8 and 12 μg of purified translation factors to a 10 μL CFPS reaction increases protein yield by ~2-fold. Supplementation of up to 17 μg of purified protein does not result in any further increase. Reaction assembly, purified protein supplementation, and incubation conditions are described in Methods, Sections M3&M6. Data are presented as mean values & error bars represent s.d. (n=4 independent experiments). Standard two-tail t-test. Source data for FIGS. 2B&C are provided as a Source Data file.

FIGS. 3A-F: Mass spectrometry reveals proteome reprogramming

3A) Expression data of all extracts used in mass spectrometry analysis. Data are presented as mean values & error bars represent s.d. (n=6 three independent reactions of two independent extract preparations). Standard two-tail t-test.

3B) Principal component analysis showing the grouping of the various extracts based on their protein profile. Ellipses indicate the boundary for statistical significance by a two-tailed t-test (p-value <0.01). Clear grouping is observed between the replicates of each sample.

3C) Volcano plots displaying the changes in protein intensity between each extract and the BL21(DE3) control. Red data points indicate a decrease in protein intensity greater than 25% and a p-value <0.01 from a two-sided t-test. Blue data points indicate an increase in protein intensity greater than 25% and a p-value <0.01 form a two-tailed t-test. The proteins that were intentionally overexpressed are colored black. Numerous statistically significant changes are observed, many of which are downregulated.

3D) The sum of protein intensity in each category for each extract is presented as percentages of the total protein intensity in that extract. There is a marked increase in Gene Expression and a decrease in Metabolism and Homeostasis related proteins when comparing BL-1S & BL-7S to BL-E.

3E) The identified proteins were further subdivided into more specific functional groups. The log difference between the protein intensity of each extract and BL-E were calculated and then averaged within each functional group and plotted on a colorimetric scale. The dendrogram represents the clustering of each protein group based on their similarity to other groups. CFP was inserted into the Unknown category.

3F) Diagram of translation indicating the key changes in the proteome and their influence on gene expression. FIGS. 3B-E use the same samples throughout. (n=4 two independent samples from two independent extract preparations).

FIGS. 4A-D: Enhanced CFPS as a versatile tool for the expression of diverse proteins.

4A) CFPS of ferritin using BL-7S$_{WCE}$ and BL-P$_{WCE}$. The bar chart shows that the expression of ferritin in reactions assembled using BL-7S$_{WCE}$ is ~0.5-fold higher than the expression achieved using BL-P$_{WCE}$. Standard two-tail t-test (n=3 independent experiments). Top panel: Representative SDS-PAGE results of CFPS reactions expressing ferritin (+) and negative control without plasmid (−).

4B) TEM images of ferritin nanocages. The left image shows the stained samples, while the right image shows the unstained samples. In the unstained image, the iron core of the ferritin cages can be seen. White arrows indicate nanocages. Three independent experiments of the assembly of ferritin nanocages and its imaging using TEM (See Methods, Section M9) were performed. All experiments showed the same results. Scale bar represents 100 nm.

4C) CFPS of Cas9 using BL-7S$_{WCE}$ and control extracts. The bar chart shows that the expression of Cas9 in reactions assembled using BL-7S$_{WCE}$ is ~3 and ~5-fold higher than the expression achieved using BL-E$_{WCE}$ and S30, respectively. See Methods, Section M8 for details about Cas9 quantification. Standard two-tail t-test (n=3 independent experiments). Top panel: Representative SDS-PAGE results of CFPS reactions expressing Cas9 (+) and negative control without plasmid (−).

4D) CFPS of deGFP using linear DNA as a template. The reactions assembled using 1:1 and 1:5 inoculation ratios of BL-Gam$_{WCE}$ and linear DNA as a template show a 74% and 24% of deGFP expression respectively compared to a control assembled using BL-7S$_{WCE}$ and plasmid DNA as a template. These reactions exhibit up to ~2-fold higher deGFP expression than controls assembled using BL-7S$_{WCE}$ and linear DNA as a template. Standard two-tail t-test (n=4 independent experiments).

Figure 4A:
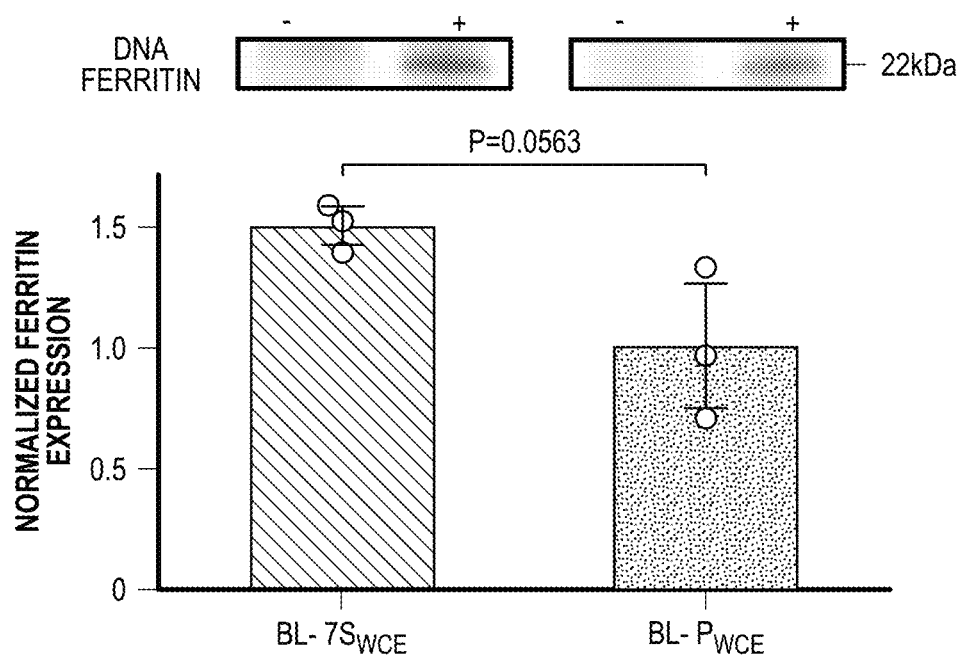

FIGS. 4A, C&D data are presented as mean values & error bars represent s.d.

DEFINITIONS

A polynucleotide sequence is "heterologous" or "exogenous" to an organism or a second polynucleotide sequence if it originates from a foreign species, or, if from the same species, is modified from its original form. For example, when a promoter is said to be operably linked to a heterologous coding sequence, it means that the coding sequence is derived from one species whereas the promoter sequence is derived another, different species; or, if both are derived from the same species, the coding sequence is not naturally associated with the promoter (e.g., is a genetically engineered coding sequence, e.g., from a different gene in the same species, or an allele from a different ecotype or variety).

An "expression cassette" refers to a nucleic acid construct that, when introduced into a host cell, results in transcription and/or translation of an RNA or polypeptide, respectively. In the case of both expression of transgenes, the inserted polynucleotide sequence need not be identical, but may be only substantially identical to a sequence of the gene from which it was derived.

The term "host cell" refers to any cell capable of replicating and/or transcribing and/or translating a heterologous polynucleotide. Thus, a "host cell" refers to any prokaryotic cell (including but not limited to *E. coli*) or eukaryotic cell (including but not limited to yeast cells, mammalian cells, avian cells, amphibian cells, plant cells, fish cells, and insect cells), whether located in vitro or in vivo. For example, host cells may be located in a transgenic animal or transgenic plant. prokaryotic cell (including but not limited to *E. coli*) or eukaryotic cells (including but not limited to yeast cells, mammalian cells, avian cells, amphibian cells, plant cells, fish cells, and insect cells). Host cells can be for example, transformed with heterologous polynucleotide.

"Cell-free" means that a cell lysate contains no cells or less than 0.001% or 0.0001% of cells compared to the cell mixture just prior to lysing. In some embodiments, a cell lysate has fewer than 1000, 100, or 10 cells.

"Operably linked" indicates that two or more DNA segments are joined together such that they function in concert for their intended purposes. For example, coding sequences are operably linked to promoter in the correct reading frame such that transcription initiates in the promoter and proceeds through the coding segment(s) to the terminator.

A "polynucleotide" is a single- or double-stranded polymer of deoxyribonucleotide or ribonucleotide bases typically read from the 5' to the 3' end. Polynucleotides include RNA and DNA, and may be isolated from natural sources, synthesized in vitro, or prepared from a combination of natural and synthetic molecules. When the term is applied to double-stranded molecules it is used to denote overall length and will be understood to be equivalent to the term "base pairs".

A "polypeptide" or "protein" is a polymer of amino acid residues joined by peptide bonds, whether produced naturally or synthetically. Polypeptides of less than about 75 amino acid residues are also referred to here as peptides or oligopeptides.

The term "promoter" is used herein for its art-recognized meaning to denote a portion of a gene containing DNA sequences that provide for the binding of RNA polymerase and initiation of transcription of an operably linked coding sequence. Promoter sequences are typically found in the 5' non-coding regions of genes.

The terms "identical" or percent "identity," in the context of two or more nucleic acids or polypeptide sequences, (e.g., two proteins of the invention and polynucleotides that encode them) refer to two or more sequences or subsequences that are the same or have a specified percentage of amino acid residues or nucleotides that are the same, when compared and aligned for maximum correspondence, as measured using one of the following sequence comparison algorithms or by visual inspection.

The phrase "substantially identical," in the context of two nucleic acids or polypeptides of the invention, refers to two or more sequences or subsequences that have at least 60%, 65%, 70%, 75%, 80%, or 90-95% nucleotide or amino acid residue identity, when compared and aligned for maximum correspondence, as measured using one of the following sequence comparison algorithms or by visual inspection. Any of the translational polypeptides described herein can be expressed in a form substantially identical to the naturally-occurring translation proteins, e.g., as found in *E. coli*. Preferably, the substantial identity exists over a region of the sequences that is at least about 50 residues in length, more preferably over a region of at least about 100 residues, and most preferably the sequences are substantially identical over at least about 150 residues. In a most preferred embodiment, the sequences are substantially identical over the entire length of the coding regions.

For sequence comparison, typically one sequence acts as a reference sequence, to which test sequences are compared. When using a sequence comparison algorithm, test and reference sequences are input into a computer, subsequence coordinates are designated, if necessary, and sequence algorithm program parameters are designated. The sequence comparison algorithm then calculates the percent sequence identity for the test sequence(s) relative to the reference sequence, based on the designated program parameters.

Optimal alignment of sequences for comparison can be conducted, e.g., by the local homology algorithm of Smith & Waterman, *Adv. Appl. Math.* 2:482 (1981), by the homology alignment algorithm of Needleman & Wunsch, *J. Mol. Biol.* 48:443 (1970), by the search for similarity method of Pearson & Lipman, *Proc. Nat'l. Acad. Sci. USA* 85:2444 (1988), by computerized implementations of these algorithms (GAP, BESTFIT, FASTA, and TFASTA in the Wisconsin Genetics Software Package, Genetics Computer Group, 575 Science Dr., Madison, Wis.), or by visual inspection (see generally, *Current Protocols in Molecular Biology*, F. M. Ausubel et al., eds., Current Protocols, a joint venture between Greene Publishing Associates, Inc. and John Wiley & Sons, Inc., (1995 Supplement) (Ausubel)).

BLAST and BLAST 2.0 algorithms are suitable for determining percent sequence identity and sequence similarity and are described in Altschul et al. (1990) *J Mol. Biol.* 215: 403-410 and Altschuel et al. (1977) *Nucleic Acids Res.* 25: 3389-3402, respectively. Software for performing BLAST analyses is publicly available through the National Center for Biotechnology Information (http://www.ncbi.nlm.nih-.gov/). This algorithm involves first identifying high scoring sequence pairs (HSPs) by identifying short words of length W in the query sequence, which either match or satisfy some positive-valued threshold score T when aligned with a word of the same length in a database sequence. T is referred to as the neighborhood word score threshold (Altschul et al, supra). These initial neighborhood word hits act as seeds for initiating searches to find longer HSPs containing them. The word hits are then extended in both directions along each sequence for as far as the cumulative alignment score can be increased. Cumulative scores are calculated using, for nucleotide sequences, the parameters M (reward score for a pair of matching residues; always >0) and N (penalty score for mismatching residues; always <0). For amino acid sequences, a scoring matrix is used to calculate the cumulative score. Extension of the word hits in each direction are halted when: the cumulative alignment score falls off by the quantity X from its maximum achieved value; the cumulative score goes to zero or below, due to the accumulation of one or more negative-scoring residue alignments; or the end of either sequence is reached. The BLAST algorithm parameters W, T, and X determine the sensitivity and speed of the alignment. The BLASTN program (for nucleotide sequences) uses as defaults a wordlength (W) of 11, an expectation (E) of 10, M=5, N=−4, and a comparison of both strands. For amino acid sequences, the BLASTP program uses as defaults a wordlength (W) of 3, an expectation (E) of 10, and the BLOSUM62 scoring matrix (see Henikoff & Henikoff, *Proc. Natl. Acad. Sci. USA* 89:10915 (1989)).

In addition to calculating percent sequence identity, the BLAST algorithm also performs a statistical analysis of the similarity between two sequences (see, e.g., Karlin & Altschul, *Proc. Nat'l. Acad. Sci. USA* 90:5873-5787 (1993)). One measure of similarity provided by the BLAST algorithm is the smallest sum probability (P(N)), which provides an indication of the probability by which a match between two nucleotide or amino acid sequences would occur by chance. For example, a nucleic acid is considered similar to a reference sequence if the smallest sum probability in a comparison of the test nucleic acid to the reference nucleic acid is less than about 0.1, more preferably less than about 0.01, and most preferably less than about 0.001.

DETAILED DESCRIPTION OF THE INVENTION

This application describes methodologies for preparation of a bacterial whole cell lysate with higher protein expression than naturally-commercially available whole cell lysates, e.g., from cells that naturally express protein expression polypeptides. Surprisingly, it has been discovered that cell lysates can be used from cells overexpressing translational proteins. The method described here comprises steps for the preparation of the whole cell lysate using an bacterial (e.g., *Escherichia coli*) consortium overexpressing the translational proteins required for in vitro protein translation. This allows both the production of an excess of translation machinery (polypeptides) and the adaptation of the host proteome for a more efficient translation system. The method also provides culture conditions, lysis, processing of this microbial consortium and buffer preparations to prepare this high-yield whole cell lysate.

The proteins in the cell lysate may comprise initiation factors, elongation factors, termination/release factors, ribosome recycling factor (also known as ribosome release factor or RRF) and optionally one or more of tRNA-Amino acyl-transferases. By over expressing (expressing at levels higher than naturally occur) these protein translation polypeptides, the resulting cell lysates will in some embodiments comprise a higher level of one or more (e.g., each) of the polypeptides (e.g., due to recombinant expression) compared to a wildtype (non-recombinant control bacterial cell). Exemplary polypeptides, as well as other details of their expression, can be found in PCT/US2018/017102, which is incorporated by reference for all purposes. In some embodiments, the initiation factors are selected from 1, 2, or 3 of translational initiation factor 1, translational initiation factor 2, and translational initiation factor 3; the elongation factors are selected from 1, 2, 3, or 4 of translational elongation factor G, translational elongation factor Tu, translational elongation factor Ts, and translational elongation factor 4; the termination/release factors are selected from 1, 2 or 3 of translational release factor 1, translational release factor 2, and translational release factor 3. In general it is not believed that heterologous expression of a tRNA-Amino acyl-transferase is needed to obtain desired levels of protein translation. However, in some embodiments, one or more or all of the following tRNA-Amino acyl-transferases are heterologously expressed in the cell mixture: Val-tRNA transferase, Met-tRNA transferase, Ile-tRNA transferase, Thr-tRNA transferase, Lys-tRNA transferase, Glu-tRNA transferase, Ala-tRNA transferase, Asp-tRNA transferase, Asn-tRNA transferase, Leu-tRNA transferase, Arg-tRNA transferase, Cys-tRNA transferase, Trp-tRNA transferase, Phe-tRNA transferase B, Pro-tRNA transferase, Ser-tRNA transferase, Phe-tRNA transferase A, Gln-tRNA transferase, Tyr-tRNA transferase, Met-tRNA formyltransferase, Gly-tRNA transferase B, His-tRNA transferase, and Gly-tRNA transferase A, each from *E. coli* or other bacterial cell.

The cell lysates can include one or more nuclease inhibitor, for example to reduce degradation of an added exogenous polynucleotide (DNA or RNA) that is to be translated. An exemplary nuclease inhibitor is the bacteriophage λ Gam protein. The nuclease inhibitor can be added as a purified protein to the cell lysate of the nuclease inhibitor can be expressed in one or more cell from the cell mixture and thus will be present in the cell lysate.

Methods of making a cell lysate comprising the translation polypeptides are also provided herein. In some embodiments, the methods comprise (a) providing a microbial culture comprising a plurality of different cells, wherein different cells heterologously express one or more of the polypeptides such that the cell mixture as a whole expresses each of the polypeptides. In some embodiments, different cells in the mixture comprise one or more recombinant expression cassette encoding one or more different protein involved in translation of mRNA, wherein the protein expression level of each protein is controlled to a predefined level, such that the proteins are capable of forming a multi-protein complex; and (b) subsequently cells in the mixture are lysed to form a cell lysate. The cells are lysed by any method that lyses cells while not significantly harming the ability of the translational polypeptides to allow for translation of proteins. The cells expressing the different translational polypeptides can be cultured together in a mixture and then lysed together in the mixture or the cells can be cultured and lysed separately, and the resulting lysates can then be mixed to form a cell lysate mixture comprising all of (or 2, 3, 4, 5, 6, 7, 8, 9, or 10 of) the translational polypeptides, e.g., at least translational initiation factor 1 (IF1); translational initiation factor 2 (IF2); translational initiation factor 3 (IF3); translational elongation factor G (EF-G); translational elongation factor Tu (EF-Tu); translational elongation factor Ts (EF-Ts); translational elongation factor 4 (EF4); translational release factor 1 (RF1), translational release factor 2 (RF2), translational release factor 3 (RF3); and ribosome recycling factor (RRF); and optionally further including Ala-tRNA transferase. In some embodiments, the heterologously expressed polypeptides comprise ro consist of translational initiation factor 1 (IF1); translational initiation factor 2 (IF2); translational initiation factor 3 (IF3); translational elongation factor G (EF-G); translational elongation factor Tu (EF-Tu); translational elongation factor Ts (EF-Ts); translational elongation factor 4 (EF4); translational release factor 1 (RF1), translational release factor 3 (RF3); and ribosome recycling factor (RRF); and optionally further including Ala-tRNA transferase, translational release factor 2 (RF2), or both.

Further provided are methods of translating an mRNA molecule into a polypeptide in the lysate. The methods comprise, for example: providing a cell lysate comprising the translational polypeptides and forming a reaction mixture comprising the cell lysate and an mRNA molecule or a DNA molecule encoding the mRNA; (d) incubating the reaction mixture under conditions suitable for translation of the mRNA molecule (which is initially transcribed in embodiments in which the DNA molecule is supplied) into a polypeptide; and optionally isolating the polypeptide.

Nucleic acids encoding the polypeptides can be expressed using routine techniques in the field of recombinant genetics. Basic texts disclosing such techniques include Sambrook and Russell, Molecular Cloning, A Laboratory Manual (3rd ed. 2001); Kriegler, Gene Transfer and Expression: A Laboratory Manual (1990); and Current Protocols in Molecular Biology (Ausubel et al., eds., 1994-1999). Modifications f the polypeptides can additionally be made without diminishing biological activity. Some modifications may be made to facilitate the cloning, expression, or incorporation of a domain. The proteins of the invention can be made using standard methods well known to those of skill in the art. Recombinant expression in a variety of microbial host cells, including *E. coli*, or other prokaryotic hosts is well known in the art.

Polynucleotides encoding the desired proteins in the complex, recombinant expression vectors, and host cells containing the recombinant expression vectors, as well as methods of making such vectors and host cells by recombinant methods are well known to those of skill in the art.

The polynucleotides may be synthesized or prepared by techniques well known in the art. Nucleotide sequences encoding the desired proteins may be synthesized, and/or cloned, and expressed according to techniques well known to those of ordinary skill in the art. In some embodiments, the polynucleotide sequences will be codon optimized for a particular recipient using standard methodologies. For example, a DNA construct encoding a protein can be codon optimized for expression in microbial hosts, e.g., bacteria.

Examples of useful bacteria include, but are not limited to, *Escherichia, Enterobacter, Azotobacter, Erwinia, Bacillus, Pseudomonas, Klebsiella, Proteus, Salmonella, Serratia, Shigella, Rhizobia, Vitreoscilla,* and *Paracoccus*. The nucleic acid encoding the desired protein is operably linked to appropriate expression control sequences for each host. For *E. coli* this can include, for example, a promoter such as the T7, trp, or lambda promoters, a ribosome binding site and preferably a transcription termination signal. The proteins may also be expressed in other cells, such as mammalian, insect, plant, or yeast cells.

Commonly used prokaryotic control sequences, e.g., promoters for transcription initiation, optionally with an operator, along with ribosome binding site sequences, include such commonly used promoters as the beta-lactamase (penicillinase) and lactose (lac) promoter systems (Change et al., Nature (1977) 198: 1056), the tryptophan (trp) promoter system (Goeddel et al., Nucleic Acids Res. (1980) 8: 4057), the tac promoter (DeBoer, et al., Proc. Natl. Acad. Sci. U.S.A. (1983) 80:21-25); and the lambda-derived PL promoter and N-gene ribosome binding site (Shimatake et al., Nature (1981) 292: 128). The particular promoter system is not critical; any available promoter that functions in prokaryotes and provides the desired level of activity can be used. Standard bacterial expression vectors include plasmids such as pBR322-based plasmids, e.g., pBLUESCRIPT™, pSKF, pET23D, lambda-phage derived vectors, and fusion expression systems such as GST and LacZ. Epitope tags can also be added to recombinant proteins to provide convenient methods of isolation, e.g., c-myc, HA-tag, 6-His tag (SEQ ID NO: 1), maltose binding protein, VSV-G tag, anti-DYKDDDDK tag (SEQ ID NO: 2), or any such tag, a large number of which are well known to those of skill in the art.

Either constitutive or regulated promoters can be used. Regulated promoters can be advantageous because the host cells can be grown to high densities before expression of the translational polypeptides is induced. High level expression of heterologous proteins slows cell growth in some situations. An inducible promoter is a promoter that directs expression of a gene where the level of expression is alterable by environmental or developmental factors such as, for example, temperature, pH, anaerobic or aerobic conditions, light, transcription factors and chemicals. For *E. coli* and other bacterial host cells, inducible promoters are known to those of skill in the art. These include, for example, the lac promoter, the bacteriophage lambda PL promoter, the hybrid trp-lac promoter (Amann et al. (1983) Gene 25: 167; de Boer et al. (1983) Proc. Nat'l. Acad. Sci. USA 80: 21), and the bacteriophage T7 promoter (Studier et al. (1986) J. Mol. Biol.; Tabor et al. (1985) Proc. Nat'l Acad. Sci. USA 82: 1074-8). These promoters and their use are also discussed in Sambrook et al., supra.

Translational coupling may be used to enhance expression. The strategy uses a short upstream open reading frame derived from a highly expressed gene native to the translational system, which is placed downstream of the promoter, and a ribosome binding site followed after a few amino acid codons by a termination codon. Just prior to the termination codon is a second ribosome binding site, and following the termination codon is a start codon for the initiation of translation. The system dissolves secondary structure in the RNA, allowing for the efficient initiation of translation. See Squires, et. al. (1988), J. Biol. Chem. 263: 16297-16302.

The construction of translational polypeptides described here can involve the use of vectors able to replicate in bacteria. Such vectors are commonly used in the art. Kits are commercially available for the purification of plasmids from bacteria (for example, EasyPrep™, FlexiPrep™, from Pharmacia Biotech; StrataClean™, from Stratagene; and, QIAexpress® Expression System, Qiagen). The isolated and purified plasmids can then be further manipulated to produce other plasmids, and used to transform cells.

EXAMPLES

The following examples are offered to illustrate, but not to limit the claimed invention.

Here, we apply the holistic synthetic biology approach to the engineering of cell-free protein synthesis (CFPS) systems. CFPS decouples cellular growth from protein production, allowing for applications such as synthesis of toxic or metabolically interfering proteins [Lim, H. J. et al., *Biotechnol. Biofuels* 9, 1-7 (2016); Thoring, L et al., *Sci. Rep.* 7, 1-15 (2017)] paper-based diagnostics [Pardee, K. et al., *Cell* 159, 940-954 (2014); Takahashi, M. K. et al., *Nat. Commun.* 9, 1-12 (2018)], a priori prediction of metabolic burden [Borkowski, O. et al., *Nat. Commun.* 9, (2018)] and function of genetic circuits [Chappell, J., Jensen, K. & Freemont, P. S., *Nucleic Acids Res.* 41, 3471-3481 (2013); Sun, Z. Z. et al., *ACS Synth. Biol.* 3, 387-397 (2014)], high-throughput screening [Contreras-Llano, L. E. & Tan, C., Synth. Biol. 3, (2018)], and construction of artificial cells [Ding, Y. et al., *ACS Appl. Mater. Interfaces* 10, 30137-30146 (2018)]. To produce CFPS, cells are grown to mid-exponential phase and then lysed to produce the whole-cell extract. The resulting cell lysate is then used in CFPS reactions by supplementing it with salts, energy sources, amino acids, and dNTPs. Attempts to improve CFPS have focused on the deletion of proteins that drain resources from CFPS, including nucleases [Hong, S. H. et al., *ChemBioChem* 16, 844-

853 (2015); Schoborg, J. A et al., *Synth. Syst. Biotechnol.* 1, 2-6 (2016)], proteases [Jiang, X. et al., *J. Biosci. Bioeng.* 93, 151-156 (2002); Goerke, A. R. et al., *Metab. Eng.* 10, 187-200 (2008)], and enzymes involved in amino acid metabolism [Michel-Reydellet, N., Calhoun, K. & Swartz, J., *Metab. Eng.* 6, 197-203 (2004); Calhoun, K. A. & Swartz, J. R., 193-203 (2006)]. Purified proteins, such as molecular chaperones [Tsalkova, T. et al., *Biochemistry* 32, 3377-3380 (1993); Ying, B. W., Taguchi, H., Kondo, M. & Ueda, T., *J. Biol. Chem.* 280, 12035-12040 (2005); Niwa, T., Kanamori, T., Ueda, T. & Taguchi, H, *Proc. Natl. Acad. Sci. U.S.A* 109, 8937-8942 (2012); Agashe, V. R. et al., *Cell* 117, 199-209 (2004)], transcription and translation machinery [Underwood, K. A., Swartz, J. R. & Puglisi, J. D., *Biotechnol. Bioeng.* 91, 425-435 (2005); Zhang, Y. et al., *Biochem. Eng. J.* 138, 47-53 (2018)], have also been added to CFPS reactions. In addition, genome recoding approaches have been used to modify the proteome of source bacteria through gene knock-ins [Des Soye, B. J. et al., *Cell Chem. Biol.* 26, 1743-1754.e9 (2019)] or knock-outs [Martin, R. W. et al., *Nat. Commun.* 9, 1203 (2018)]. While these approaches can precisely change the concentration of a few proteins, they are challenging to scale up for targeting multiple pathways that can impact CFPS. Furthermore, manipulating the expression levels of many essential genes while maintaining cell viability is often inhibitively complex.

Results

Enhanced CFPS via overexpression of translation machinery. To implement the holistic approach, we used synthetic modules to express all or a subset of the 34 proteins of the core *E. coli* translation machinery within multiple strains of *E. coli* BL21 (DE3) that were lysed and used in CPFS. Distribution of protein overexpression across multiple strains was chosen to decrease the metabolic burden caused by protein expression and plasmid maintenance. The burden imposed by plasmid maintenance manifests in the form of decreased growth rates [Rozkov, A. et al., *Biotechnol. Bioeng.* 88, 909-915 (2004)], which in turn generates lower concentrations of ribosomes and other translation machinery proteins [Bosdriesz, E. et al., *FEBS J.* 282, 2029-2044 (2015)]. This has been shown to be a limiting factor for efficient CFPS [Underwood, K. A., Swartz, J. R. & Puglisi, J. D., *Biotechnol. Bioeng.* 91, 425-435 (2005)]. We hypothesized that the overexpression of translation machinery should benefit CFPS in two ways. First, it should compensate for the increased metabolic burden by virtue of being supplied with translation factors. And second, it should shift the global proteome to a high-growth-rate-like state where translation factors are enriched, and the cell reaches peak protein synthesis efficiency. We produced two different microbial consortia, one with 18 strains (BL-18S) and the other with 7 strains (BL-7S) to obtain cell lysates enriched in translation machinery without the need to purify and supplement individual proteins. BL-18S expressed 11 Initiation, Elongation, and Termination factors (IETs), as well as 23 Aminoacyl-tRNA transferases (AAT). BL-7S expressed 11 IETs and 1 AAT (FIG. 1A, Supplementary Table 1). Throughout this study, we used the expression level of deGFP, a truncated version of eGFP with the same fluorescence properties [Shin, J. & Noireaux, V., *J. Biol. Eng.* 4, 2-10 (2010)] to quantify the absolute yield of the CFPS (Methods, Section M4, and Supplementary Note 1). In addition, we optimized the reaction buffer and lysate preparation for the new CFPS (Supplementary Note 2).

To compare our modified extracts to existing systems, we ran several experiments to quantify the differences. The whole-cell lysate of BL-18S (BL-18S$_{WCE}$) and BL-7S (BL-7S$_{WCE}$) had comparable expression activities. Thus, we proceeded with BL-7S$_{WCE}$ due to its simpler preparation procedure. To assess the influence of translation machinery overexpression in CFPS, we compared the protein yield against a cell lysate produced using *E. coli* BL21(DE3) without any plasmids (BL-E$_{WCE}$), a cell lysate from the same strain carrying the original plasmid vectors (BL-P$_{WCE}$), and the commercial S30 T7 High-Yield Expression System (Promega Corporation) (S30) (Methods, Section M2). In batch reaction mode, BL-7S$_{WCE}$ produced a maximum of 1.51 mg mL$^{-1}$ of deGFP (FIG. 1B), and 4.8 mg mL$^{-1}$ in a semi-continuous exchange mode (FIG. 1C). The S30 expression system performed poorly when adapted to the semi-continuous exchange mode. Therefore, the data were not included because the protocol for this setup was not defined by the manufacturer. The yields of BL-7S$_{WCE}$ were 2 to 3-fold higher than the controls in both formats. When examining the expression dynamics (FIG. 1D), CFPS reactions assembled using our in-lab cell-lysates show a 20 minutes lag-period before the production of deGFP can be detected. During this initial lag period, the transcription machinery (T7 RNAP) likely ramped up mRNA synthesis until the mRNA reached the concentration necessary for starting protein synthesis. Once protein synthesis was started, reactions assembled using BL-7S$_{WCE}$ expressed deGFP at a higher rate than other cell-lysates. Altogether, the data show that BL-7S$_{WCE}$ can achieve higher expression levels than conventional systems.

Effect of translation machinery concentration on CFPS. Our next set of experiments are intended to investigate the cause of the improved CFPS efficiency. Specifically, we sought to decouple the direct effect of increasing the translation factor concentrations in the CFPS reaction from the indirect effects of protein overexpression and feedback from the overexpressed proteins. To study the effects of the increased translation factors in a standard CFPS reaction, we purified the translation machinery proteins overexpressed in BL-18S and supplemented it to BL-E$_{WCE}$ (FIG. 2A, Methods, Sections M3&M6). The expression level of deGFP increased proportionally with the addition of translation machinery (FIG. 2B). These results demonstrate that the increased concentration of protein machinery is not the only factor responsible for the increased protein expression of our multi-strain CFPS systems. Furthermore, we intended to rule out any additional effects that plasmid maintenance or protein overexpression could be causing in our multi-strain CFPS systems. To rule out the plausible effects, we purified translation machinery proteins (overexpressed in BL-7S) and supplemented them to an extract that was generated from BL21 (DE3) over-expressing Cyan Fluorescent Protein (CFP) (BL-CFP$_{WCE}$; Methods, Sections M2, M3&M6). The expression level once again increased proportionally with the amount of protein added but plateaued at a 2-fold increase (FIG. 2C). Our results show that while the concentrations of translation machinery are comparable between single-strain preparations supplemented with purified translation machinery and multi-strain preparations (Supplementary Note 3.), the yields obtained in CFPS are not equivalent. These results are consistent with our hypothesis that the overexpression of translation machinery causes an auxiliary effect on the host circuits that create an environment more favorable for CFPS.

Figure 3A:
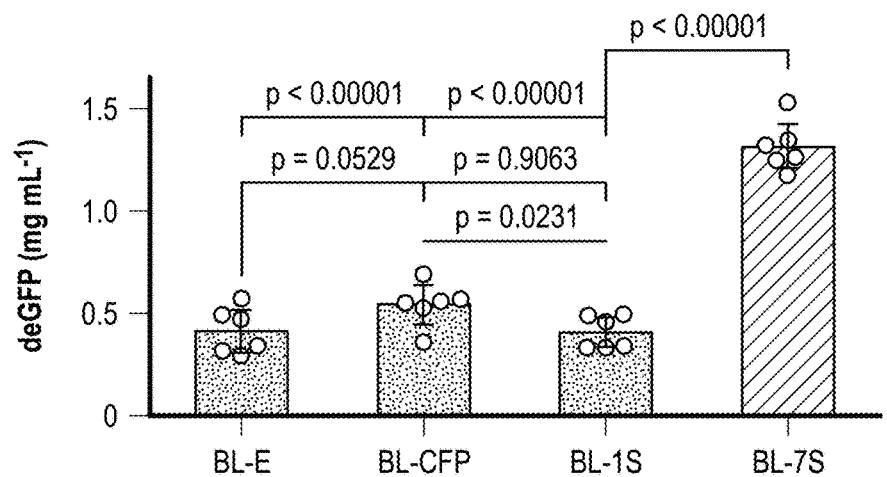
Figure 3B:
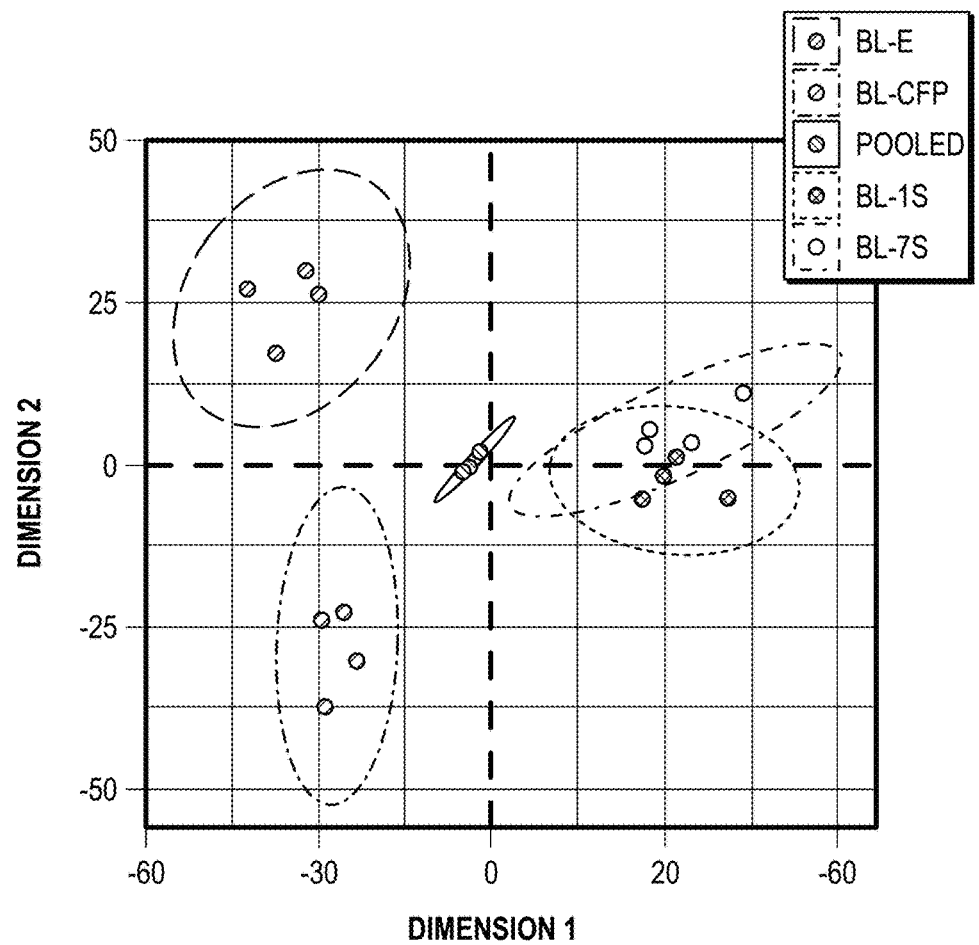
Figure 3C:
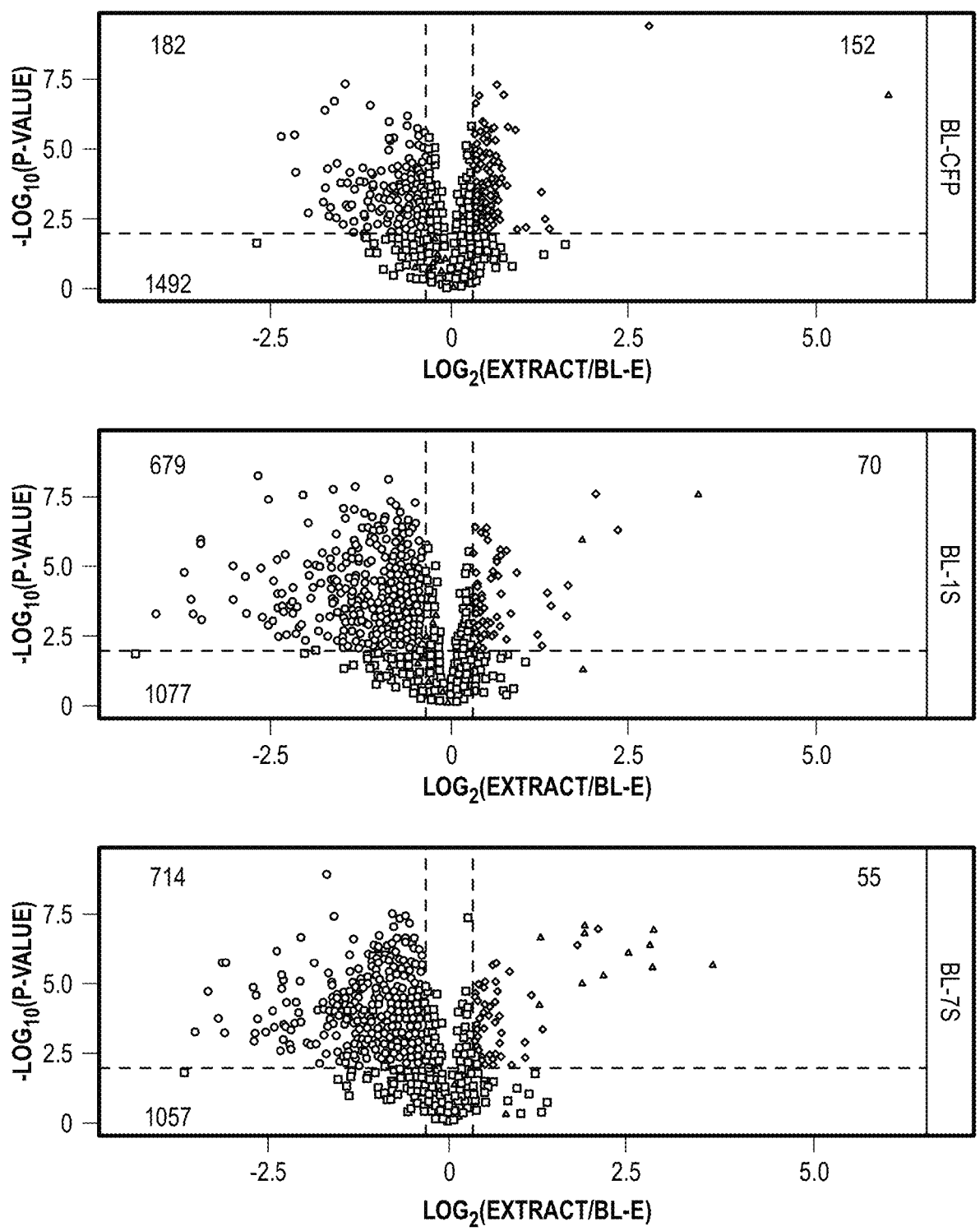

Influence of protein overexpression on the host proteome. The above results suggest that the protein profile in our BL-7S$_{WCE}$ is more amenable to CFPS than any of the controls. Specifically, our data indicate that this proteome reprogramming occurs directly as a result of the overexpression of translation machinery by our synthetic modules. To further understand the favorable changes occurring in BL-7S, we analyzed the protein composition of several whole-cell lysates through mass spectrometry (Methods, Section M7). For this experiment, an additional extract using one of the IET strains was created, specifically Strain-1 that overexpresses the elongation factors EF-Tu and EF-Ts (BL-1S$_{WCE}$). We decided to analyze Strain 1 of our 7-strain consortium due to the major roles of EF-Tu and EF-Ts for increasing elongation rates in CFPS [Underwood, K. A., Swartz, J. R. & Puglisi, J. D., *Biotechnol. Bioeng.* 91, 425-435 (2005); Zhang, Y. et al., *Biochem. Eng. J.* 138, 47-53 (2018)], and because it represents 50% of the inoculation mixture (Supplementary Table 1). All four extracts (BL-7S$_{WCE}$, BL-1 S$_{WCE}$, BL-CFP$_{WCE}$, & BL-E$_{WCE}$) were digested, labeled, and subjected to Tandem Mass Tag (TMT) mass spectrometry in quadruplicate (Methods, Section M7). The expression capacity of these four extracts agreed with previous results (FIG. 3A). The mass spectrometry data revealed the levels of 2000 different *E. coli* proteins in all samples. After internal reference scaling (Methods, Section M7), the data were analyzed by principal component analysis (PCA), showing clear clustering of replicates and separation of experimental conditions (FIG. 3B). The results also show the expected enrichment of overexpressed CFP and translational machinery (FIG. 3C, Supplementary Note 4).

BL-7S indeed showed a global difference in protein content compared to the controls. The proteome of BL-E and BL-CFP were clustered separately in the PCA (FIG. 3B), while the clusters of BL-7S and BL-1S overlapped partly. The overlap between the proteome of BL-7S and BL-1S was anticipated because Strain-1 makes up a majority of BL-7S. To investigate the proteome changes that underlie the clustering, we plotted the fold change of each protein intensity compared to BL-E and the p-value from a two-way t-test of that comparison (FIG. 3C). On the one hand, the proteome of BL-CFP remained mostly unchanged with a nearly even split between the number of up and down regulated proteins (changes greater than 25%, p<0.01). On the other hand, the proteome of BL-7S and BL-1S showed a decrease in over a third of all observed proteins, while less than 5% of all proteins were up regulated. Even though BL-CFP showed a proteome shift, likely caused by the metabolic burden of protein overexpression, the proteome change did not boost the yield of BL-CFP$_{WCE}$. These results show that the proteome of BL-7S was affected by the expression of the translational machinery. This change in protein profile and content likely results in the generation of an environment more favorable for CFPS synthesis.

Figure 3D:
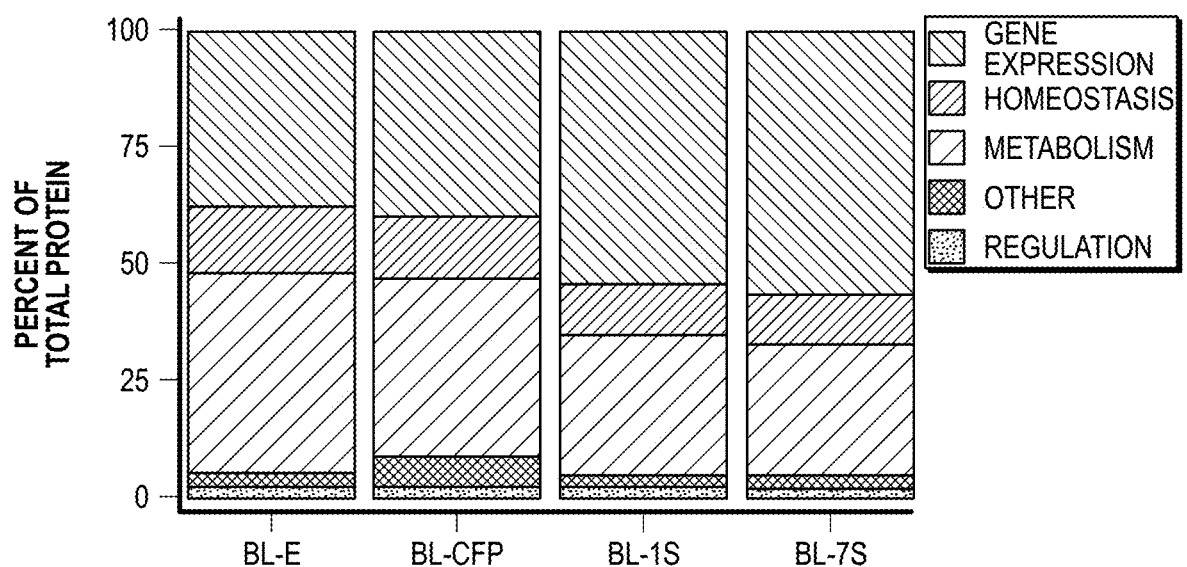
Figure 3E:
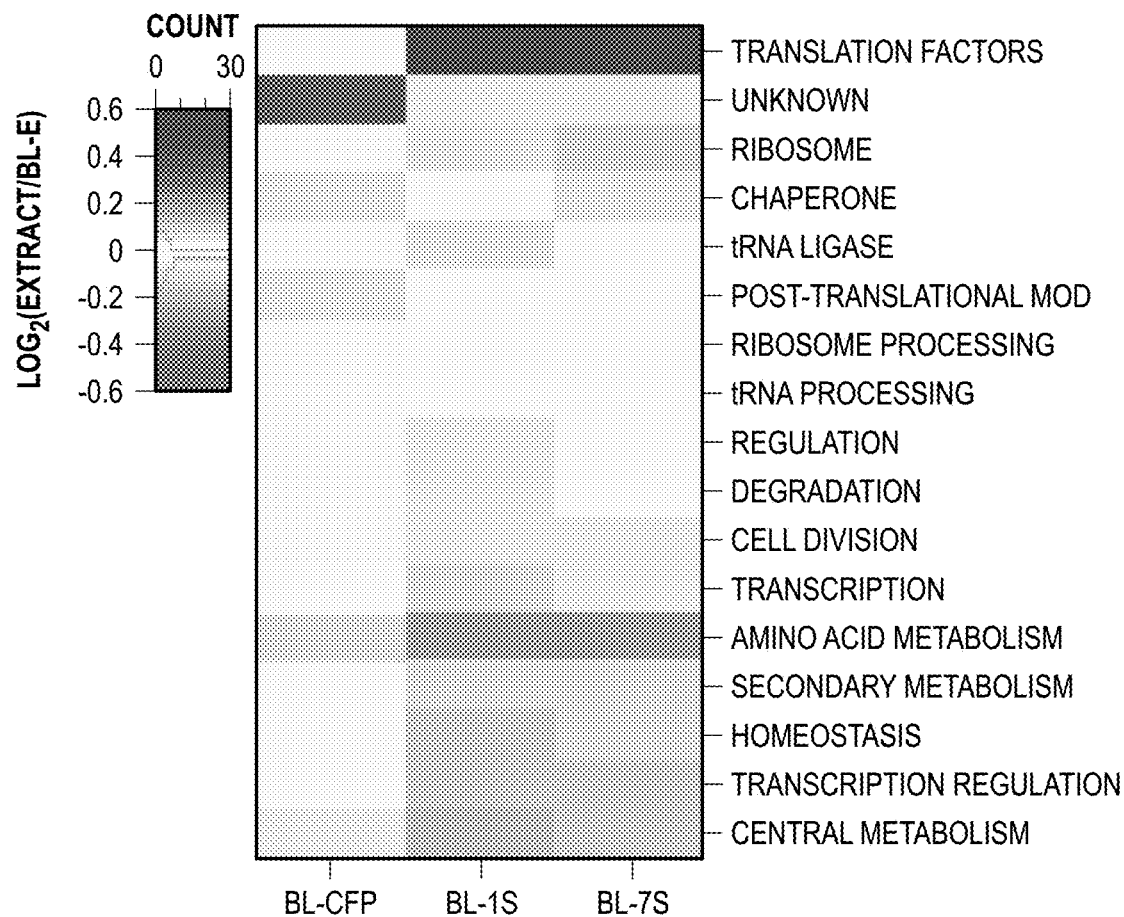
Figure 3F:
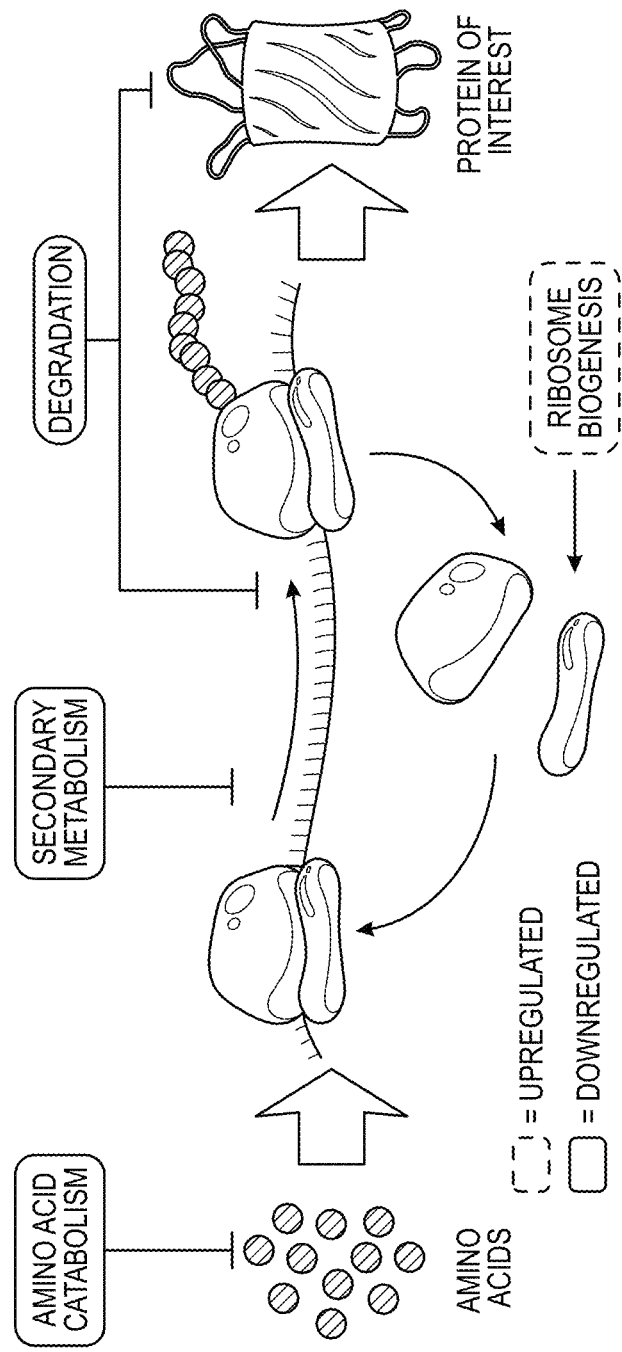

We further characterized the proteome change uncovered by our mass spectrometry results. To this end, we categorized each protein based on their assigned gene ontological function (Methods, Section M7). We then summed the intensity of each protein in each category for protein content comparison (FIG. 3D). Again, the proteome of BL-CFP and BL-E exhibited no significant difference. However, BL-7S and BL-1S exhibited a 17% increase in the Gene Expression category (e.g., translation factors, amino-acyl tRNA synthetases, ribosomes). They also showed a decrease of 14% in the metabolism (e.g., TCA cycle, amino acid catabolism) and 3% in the homeostasis (e.g., iron homeostasis, proteases, cell cycle regulators) categories. To better understand the specific proteome changes, more detailed functions were assigned to the proteins. The fold changes between the means of each protein in each extract were compared to the BL-E control. The proteins were then grouped by their function, and the average of all the fold changes was calculated (FIG. 3E). The results show that the expression of translation machinery from a local genetic module results in a global proteome shift generally associated with a cellular state at high growth rates [Bosdriesz, E. et al., *FEBS J.* 282, 2029-2044 (2015); Rozkov, A. et al., *Biotechnol. Bioeng.* 88, 909-915 (2004)]: upregulation of proteins involved in macromolecule synthesis (e.g., chaperones and ribosomal proteins); and downregulation of metabolic proteins that compete with nutrients in cell-free protein synthesis (e.g., tryptophanase and pyruvate kinase) (FIG. 3F). However, we note some exceptions to this general expectation, such as increases in a few metabolic proteins, including glycerol-3-phosphate acyltransferase and 2,3-dihydroxybenzoate-AMP ligase (Supplementary Note 4).

Figure 4B:
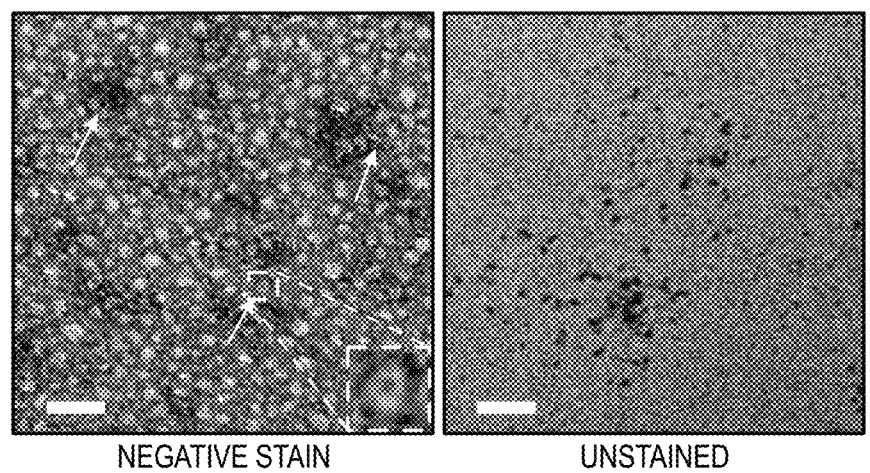

Demonstrating the versatility of enhanced CFPS. To explore the potential of our BL-7S$_{WCE}$ beyond the enhanced deGFP expression (FIG. 1B), we decided to test its versatility through different applications. For our first trial, we produced ferritin from *Archaeoglobus fulgidus* (AfFtn), an archaeal iron storage protein capable of self-assembly forming nanocages. AfFtn has been shown to encapsulate and release molecular cargo [Sana, B., Johnson, E. & Lim, S., *Biochim. Biophys. Acta—Gen. Subj.* 1850, 2544-2551 (2015)]. As AfFtn requires the assembly of precisely 24 subunits of 22 kDa to form nanocages, it is a good test case for the CFPS system to produce large protein assemblies while maintaining its function. Reactions assembled with BL-7S$_{WCE}$ expressed 50% more ferritin than our controls assembled with BL-E$_{WCE}$ (FIG. 4A). TEM images demonstrate the AfFtn nanocages of 12 nm (FIG. 4B). The iron core formation in the unstained TEM images confirms the function of the produced AfFtn.

Figures 4C, 4D:
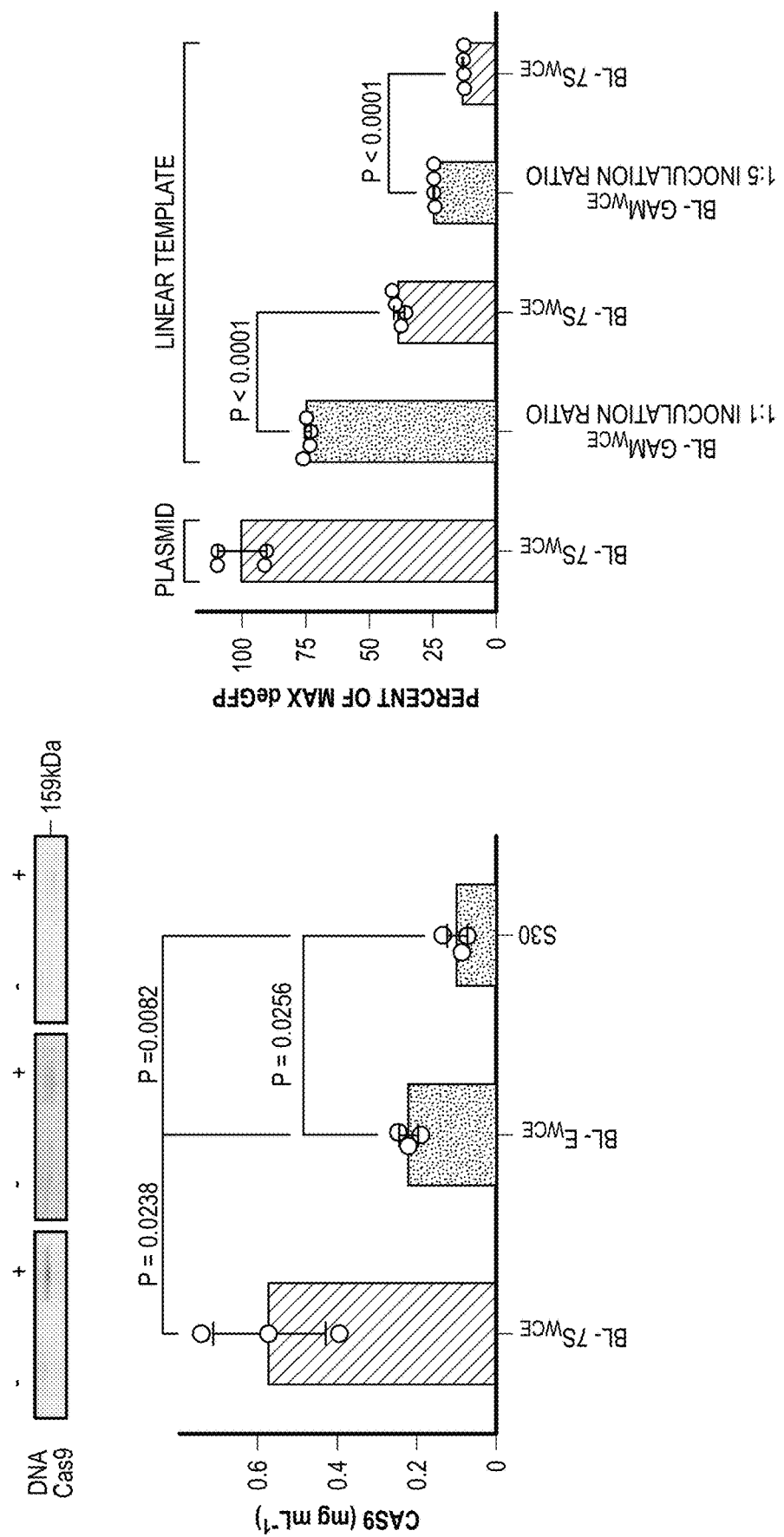

One of the major challenges of *E. coli* based CFPS systems is their limited ability to efficiently synthesize large proteins. This problem becomes particularly pronounced in the expression of proteins larger than 70 kDa [Gagoski, D. et al., *Biotechnol. Bioeng.* 113, 292-300 (2016)]. We decided to test if our multi-strain system offers an advantage over traditional approaches in this task. Thus, we expressed the biotechnologically relevant protein Cas9 (159 kDa) and compared its expression against BL-E$_{WCE}$ and S30 (FIG. 4C). Our BL-7S$_{WCE}$ produced 0.52 mg mL$^{-1}$ of Cas9. This is ~3-fold higher than BL-E$_{WCE}$ and ~5-fold higher than S30. These results show that our system can synthesize broad sizes of proteins between 20 and 160 kDa in higher quantities than conventional systems.

The modularity of the bacterial consortium enables the incorporation of additional strains in our system as a plug-and-play feature. By exploiting this feature, we could confer a new function to our cell-free system, as expressing proteins from linear templates. To implement this, we added a strain expressing the Gam protein (a nuclease inhibitor), resulting in an 8-strain WCE (BL-8S-Gam$_{WCE}$; Methods, Section M2). We used rolling circle amplification (RCA) to generate the deGFP encoding template (Methods, Section M3). The resulting double-stranded linear DNA was added directly (21% V/V) into three different cell-lysates: two BL-85-Gam$_{WCE}$ with different inoculation ratios of the Gam-expressing strain (1:1 & 1:5), and controls without Gam (BL-7S$_{WCE}$). Using the amplified linear DNA, the two BL-85-Gam$_{WCE}$ synthesized ~2-fold more deGFP than the BL-7S$_{WCE}$ controls (FIG. 4D). The deGFP expression levels increased proportionally with the amount of Gam-expressing strain. The maximum yield achieved using the linear template in reactions assembled with BL-85-Gam$_{WCE}$ is approximately 75% of the possible yield achieved using BL-7S$_{WCE}$ and plasmid template (FIG. 4C). The results of this experiment show how the modularity of our bacterial consortium approach can be exploited to custom modify cell-lysates to match the requirements of a given experiment. However, further optimization and benchmarking may be necessary to make a fair comparison between our and commercial CFPS systems that are designed for specific applications. Altogether, these applications demonstrate the power of our holistic synthetic biology approach in generating versatile high-yield CFPS systems.

Discussion

Our work highlights both the utility and the potential of holistic synthetic biology approaches in boosting the performance of local synthetic modules. We demonstrate that the proteome reprogramming described in our study is the direct result of the overexpression of translation machinery in the host cells. Furthermore, we show that the use of a plasmid system in the source strain does not result in a decrease in the activity of the CFPS system. This illustrates how plasmid-based approaches can be implemented to functionalize cell lysates without sacrificing CFPS efficiency. This study opens a new research direction in cell-free synthetic biology, showcasing how the integration of orthogonal circuits, cell physiology, and systems biology can become a powerful tool that maximizes the output of a given cell-free system. Similar approaches have been used for transcriptional rewiring with the aim of increasing the production of proteins and metabolites in vivo [Michalodimitrakis, K. & Isalan, M., *FEMS Microbiol. Rev.* 33, 27-37 (2009); Windram, 0. P. F. et al., *Nucleic Acids Res.* 45, 4984-4993 (2017)]. However, in order to refine holistic and transcriptional rewiring approaches, there are still many challenges ahead. For instance, precise molecular details of the feedback loop generated by these approaches are not fully elucidated. Understanding precisely how these positive feedback loops work could allow precise control over the targeted metabolic pathways, and tight regulation of individual protein levels. If this is achieved, the possibilities for the application of such a holistic approach are vast, ranging from the engineering of mammalian cells to the control of disease development. For instance, our holistic approach can be used to accelerate other work on cell-free systems, including the incorporation of non-natural amino acids into proteins [Hong, S. H., Kwon, Y. C. & Jewett, M. C., *Front. Chem.* 2, 1-7 (2014)], post-translational protein modifications [Jaroentomeechai, T. et al., *Nat. Commun.* 9, 1-11 (2018)], ribosome engineering [Carlson, E. D. et al., *Nat. Commun.* 10, 3920 (2019)], and the production of stable and functionally folded membrane proteins [Schneider, B. et al., *Methods in molecular biology* (Clifton, N.J.) (ed. Mus-Veteau, I.) 601, 165-186 (Humana Press, 2010)]. The benefits of exploiting the beneficial crosstalk between synthetic modules and host biological programs could open a new era in synthetic biology.

Methods

M1 Construction of Plasmids and Strains. We used the plasmids pIVEX2.3d (Roche), pET15b (Novagen), pLysS (Novagen), and pSC101[Manen, D. & Caro, L., *Molecular Microbiology* 5, 233-237 (1991)] as the backbones for all our constructs. The backbones of pET15b, pLysS, and pSC101 were used to create the plasmids pIURAH, pIURCM, and pIURKL, respectively. Briefly, the three plasmids have compatible replication origins, distinct copy number, carry a NsiIIPacI cloning site downstream of a PT7-lacO hybrid promoter, and have a T7 RNAP terminator sequence. pIURAH contains the Ampicillin resistance gene/ColE1 replication origin and expresses laI, pIURCM contains the Chloramphenicol resistance gene/p15A replication origin and expresses T7 lysozyme, and pIURKL contains Kanamycin resistance gene/pSC101 replication origin. The plasmids pIURAH and pIURKL were used as backbones to generate all 34 vectors encoding translation machinery by cloning the translation machinery genes into one of these plasmids (See Supplementary Table 1). Based on previous literature [Shimizu, Y. & Ueda, T., *Cell-Free Protein Production: Methods and protocols* (eds. Endo, Y., Takai, K. & Ueda, T.) 607, 11-21 (Humana Press, 2010)], a 6×-His-tag was also added to each gene at either the N or C terminus to allow for the purification of the translation machinery proteins. The plasmids pIURAH, pIURCM, pIURKL, pET15bL-CFP, and all 34 translation machinery expressing plasmids were made by Villareal et al. [Villarreal, F. et al., *Nat. Chem. Biol.* 14, 29-35 (2018)] and are available through Addgene [https://www.addgene.org/Cheemeng_Tan/]. The construct pIVEX-deGFP was generated by PCR amplifying the sequence of deGFP from the plasmid pBEST-OR2-OR1-Pr-UTR1-deGFP-T500 (Addgene, Cat #40019) [Shin, J. & Noireaux, V., *J. Biol. Eng.* 4, 2-10 (2010)] and inserting it into the PCR amplified backbone pIVEX using Gibson Assembly (New England BioLabs, Inc). The construct pIVEX-Eps-deGFP was built as described above for the plasmid pIVEX-deGFP, but an additional epsilon sequence (TTAACTTTAA) [Takahashi, S. et al., *J. Am. Chem. Soc.* 135, 13096-13106 (2013)] was inserted between the T7 promoter and the RBS. The construct pIVEX-Eps-Cas9 was generated by PCR amplifying the sequence of Cas9 from the plasmid pwtCas9-bacteria (Addgene, Cat #44250) [Qi, L. S. et al., *Cell* 152, 1173-1183 (2013)] and inserting it into the PCR amplified backbone pIVEX-Eps using Gibson Assembly. The plasmid pIURAH-Gam was built by PCR amplifying the sequence of Gam from the plasmid pKDsgRNA-p15 (Addgene, Cat #62656) [Reisch, C. R. & Prather, K. L. J., *Sci. Rep.* 5, 1-12 (2015)] and inserting it into the PCR amplified backbone pIURAH using Gibson Assembly. All resulting plasmids were transformed into and propagated using *E. coli* Top-10 cells (Thermo Fisher Scientific).

*E. coli* BL21(DE3) is used throughout this study to build all the strains used to produce all of our cell-free lysates. The 18-translation machinery overexpressing strains were produced by transforming *E. coli* BL21(DE3) with the plasmids specified in Supplementary Table 1, and with the plasmids pIURCM, and pIURKL (only for strain 7) without expression cassettes. Each strain is designed to overexpress 1 or 2 translation machinery proteins upon IPTG induction, and all strains have antibiotic resistance to Carbenicillin, Chloramphenicol, and Kanamycin. More details about the design of the strains can be found in our previous work [Villarreal, F. et al., *Nat. Chem. Biol.* 14, 29-35 (2018)]. BL21 (DE3) was transformed with the plasmids pIURAH, pIURCM, and pIURKL without expression cassettes to generate the strain used to produce our control with antibiotic resistance to Carbenicillin, Chloramphenicol, and Kanamycin. Our CFP expressing strain was generated by transforming the plasmids pET15bL-CFP, pIURCM, and pIURKL into BL21 (DE3). Our Gam expressing strain was generated by transforming the plasmids pIURAH-Gam, pIURCM, and pIURKL into BL21 (DE3).

M2 Preparation of whole-cell extracts. For our whole-cell extract preparations, we variate the specific strain or consortium used and the inoculation ratios (ratio represent % of the strain in the total volume of the mix). Culture & induction times and all subsequent steps were made generic among all preparations.

BL-7S$_{WCE}$ & BL-18S$_{WCE}$ were prepared using the following protocol: Each strain comprising the 7 or the 18-strain consortium was individually grown in 3 mL of 2YTP media supplemented with carbenicillin/chloramphenicol/kanamycin at 37° C. with shaking at 200 rpm overnight. The overnight cultures were used to establish the BL-7S or BL-18S consortia by mixing strains at the indicated ratios (See Supplementary Table 1). The mixtures were then used to inoculate 300 mL of 2YTP supplemented with carbenicillin & kanamycin at a 1/250 dilution.

BL-E$_{WCE}$ was prepared using the following protocol: The strain BL21 (DE3) was grown in 3 mL of 2YTP media at 37° C. with shaking at 200 rpm overnight. The saturated overnight culture was then used to inoculate 300 mL of 2YTP at a 1/250 dilution.

BL-P$_{WCE}$ was prepared using the following protocol: The strain BL21 (DE3) transformed with the plasmids pIURAH, pIURCM, and pIURKL was grown in 3 mL of 2YTP media supplemented with carbenicillin/chloramphenicol/kanamycin at 37° C. with shaking at 200 rpm overnight. The saturated overnight culture was then used to inoculate 300 mL of 2YTP supplemented with carbenicillin & kanamycin at a 1/250 dilution.

BL-CFP$_{WCE}$ was prepared using the following protocol: The strain BL21 (DE3) transformed with the plasmids pET15bL-CFP, pIURCM, and pIURKL was grown in 3 mL of 2YTP media supplemented with carbenicillin/chloramphenicol/kanamycin at 37° C. with shaking at 200 rpm overnight. The saturated overnight culture was then used to inoculate 300 mL of 2YTP supplemented with carbenicillin & kanamycin at a 1/250 dilution.

BL-85-Gam$_{WCE}$ was prepared using the following protocol:: The strains comprising the 7-strain consortium, and the Gam expressing strain transformed with the plasmids pIURAH-Gam, pIURCM, and pIURKL were individually grown in 3 mL of 2YTP media supplemented with carbenicillin/chloramphenicol/kanamycin at 37° C. with shaking at 200 rpm overnight. The overnight cultures were used to establish the BL-8S consortium by mixing strains at the indicated ratios (Supplementary Table 1). The mixtures were then used to inoculate 300 mL of 2YTP supplemented with carbenicillin & kanamycin at a 1/250 dilution.

The following steps were used for all whole cell lysate preparations: The culture was incubated at 30° C., 250 rpm until the OD reached 0.15. The culture is then induced with 0.5 mM IPTG and grown until an OD of 1.0. After induction, bacteria cells were harvested and washed twice with 20 mL of Buffer A (4,000 g, 20 min, 4° C.). Buffer A contains 10 mM Tris-acetate pH 7.6, 14 mM Magnesium acetate, and 60 mM Potassium gluconate. After the final wash and centrifugation, the pelleted cells were weighed and suspended in 1 mL of Buffer A supplemented with 2 mM DTT (Thermo Fisher Scientific) per 1 g of wet cell mass. To lyse cells by sonication, freshly suspended cells were transferred into 1.5 mL microtube and placed in an ice-water bath to minimize heat damage during sonication. The cells were lysed using a Q125 Sonicator with a 2 mm diameter probe at a frequency of 20 kHz and 50% amplitude. Sonication was continued for about 27 cycles 10s ON/10s OFF. For each 0.5 mL sample, the input energy was ~1000 J. Cell lysates were centrifuged at 12,000 g for 20 min at 4° C. The supernatant was collected and incubated at 30° C. for 30 min. The resulting WCE was aliquoted and stored at −80° C.

M3 Assembly of Cell-Free Protein Synthesis reactions. The assembly of CFPS reactions for batch experiments was carried out as follows: CFPS reactions (10 μL) were assembled in 1.5 mL low protein binding microcentrifuge tubes (Thermo Scientific) by mixing the following components: 1.2 mM each of ATP and GTP; 0.85 mM each of UTP, and CTP (Promega); 34 μg mL$^{-1}$ folinic acid (Sigma-Aldrich); 170 μg mL$^{-1}$ of E. coli tRNA mixture from E. coli MRE600 (Roche); 2 mM for each of the 20 standard amino acids (Sigma-Aldrich); 0.33 mM NAD (Roche); 0.27 mM CoA (Sigma-Aldrich); 4 mM spermidine (Sigma-Aldrich); 180 mM potassium glutamate (Sigma-Aldrich); 12 mM magnesium glutamate (Sigma-Aldrich); 50 mM HEPES pH 7.6 (Sigma); 67 mM creatine phosphate (Roche); 80 μg mL$^{-1}$ Creatine Kinase (Roche); 0.64 mM cAMP (Sigma-Aldrich); 2% PEG8k (Sigma-Aldrich); 0.2 mg mL$^{-1}$ BSA; 2.7 μL (27% v/v) of cell extract, and 100 ng plasmid DNA. Each CFPS reaction was assembled on ice and incubated overnight at 30° C. with shaking at 300 rpm unless noted otherwise. As individual reagent concentrations were optimized, their optimal value listed above were used for all reactions from that point onward.

The assembly of reactions supplemented with purified translation machinery mixtures was carried out as follows: Reactions were assembled as described above and supplemented with varying amounts of purified translation machinery mixtures. For the experiments in FIG. 2B, we supplemented the 34 translation machinery proteins overexpressed in BL-18S (Methods, Section M6) to a CFPS reaction assembled with BL-E$_{WCE}$. For the experiments in FIG. 2C, we supplemented the 11 translation machinery proteins overexpressed in BL-7S (Methods, Section M6) to a CFPS reaction assembled with BL-CFP$_{WCE}$. Supplementation of proteins did not affect the final concentration of any of the components in the CFPS reactions. Negative controls were assembled using the same volume of Buffer A than the volume of supplemented translation machinery mixtures (Methods, Section M6).

The assembly of reactions under semi-continuous agitation was carried out as follows: Reactions were scaled up to 15 μL, assembled into 1.5 mL low protein binding microcentrifuge tubes, and transferred to a 384-well plate (Corning). Once all the reactions were loaded into the plate, the wells were sealed with film and the plate was loaded into an m1000Pro Infinite plate reader to measure fluorescence. Reactions were incubated at 30° C. with semi-continuous shaking at 300 rpm (30s ON, 30s OFF) for 12 h. Fluorescence was measured every 10 min and followed for 12 h. Note: The yield of all reactions carried out in 384-well plate format under semi-continuous agitation was considerably lower compared to control batch reactions carried out in parallel. This decrease in yield was consistent across all our in-lab cell lysates and points out to agitation as a crucial parameter for achieving high-yield protein expression.

The assembly of CFPS reactions using a linear template was carried out as follows: We amplified 1 ng of the plasmid pIVEX-Eps-deGFP using the commercial kit TempliPhi for rolling circle amplification (RCA) according to the manufacturer's instructions (GE Healthcare, UK). The resulting double-stranded linear DNA template was directly added (21% V/V) to CFPS reactions assembled using BL-7S$_{WCE}$ or BL-85-Gam$_{WCE}$. This is the maximum percentage by volume that we could add to the CFPS reactions without perturbing the concentrations of the rest of the components. The precise concentration of DNA obtained through RCA could not be quantified using a Nanodrop spectrophotometer. This issue is because even in the absence of input DNA, the RCA reaction yields nonspecific products. However, according to the manufacturer's indications, we estimate that the amount of double-stranded linear DNA added to each CFPS reaction is between 150-500 ng.

M4 Quantification of deGFP expression. Fluorescent measurements were taken of CFPS reactions diluted 1:50 in Dilution Buffer (50 mM HEPES pH 7.6, 4 mM spermidine, 2% PEG8k, 12 mM Magnesium Glutamate, 180 mM Potassium Glutamate, 0.4 mg mL$^{-1}$ BSA). Active deGFP protein yields were quantified by measuring fluorescence using a NanoQuant plate (Tecan) and an m1000Pro Infinite plate reader. Excitation and emission wavelength used to measure the fluorescence of deGFP were 488 and 507 nm, respectively. deGFP fluorescence units were converted to concentration using a standard curve. The curve was generated using the pure EGFP standard from Biovision. Previous studies have demonstrated that the fluorescence of deGFP and EGFP are the same and are therefore comparable [Shin, J. & Noireaux, V., *J. Biol. Eng.* 4, 2-10 (2010)]. The EGFP sample was diluted in dilution buffer and measured to generate a standard curve.

M5 Semi-continuous exchange reaction. The semi-continuous reactions were conducted using the 96-Well Equilibrium dialyzer (MWCO 10 kDa) purchased from Harvard Apparatus (Holliston, Mass.). Reactions were set up with 20 µL cell-free reactions loaded on one side of the dialyzer with 200 µL of feeding solution on the other. The feed solution has the same composition as the cell-free reaction, except the whole-cell extract was substituted with Buffer A from the whole-cell extract procedure and the DNA was substituted with water. The reaction was incubated at 30° C. with constant rotation at 0.125 Hz on a rotary axis such that the wells were inverted with each rotation. The reaction was incubated for 24 hours prior to measurement.

M6 Co-purification of translation machinery using a co-culture approach. We used two different microbial consortia (BL-18S and BL-7S) to purify the 12 (11 IETs and 1 AAT) and 34 (11 IETs and 23 AAT) translation machinery proteins exogenously added to single strain cell-lysates. For these 12 and 34 multi-protein purifications, we followed the protocol for the preparation of BL-7S$_{WCE}$ and BL-18S$_{WCE}$ respectively (Methods, Section M2), and couple them with the following steps to co-purify the proteins overexpressed by both consortia. After cell-lysis by sonication, we proceeded to clarify the cell-lysate by centrifugation at 20,000 g for 20 min at 4° C. We collected the supernatant and proceeded with the co-purification of the overexpressed proteins in the cell lysate. The following buffers were prepared in advance and stored at 4° C. for no longer than 24 hours. Buffer A contains 10 mM Tris-acetate pH 7.6, 14 mM Magnesium acetate, and 60 mM Potassium gluconate. Buffer B contains 10 mM Tris-acetate pH 7.6, 10 mM Magnesium acetate, 1 M Ammonium chloride. Buffer C contains 10 mM Tris-acetate pH 7.6, 10 mM Magnesium acetate, 500 mM Imidazole. The collected supernatant was diluted 5-fold and applied to a 1 mL HisTrap FF column (GE Healthcare Life Sciences) previously equilibrated with 10 volumes of Wash Buffer 1 (Buffer B: Buffer C, 97.5:2.5, supplemented with 2 mM DTT). The column was washed with 10 volumes of Wash Buffer 1, followed by a second washing step with 10 volumes of Wash Buffer 2 (Buffer B: Buffer C, 95:5, supplemented with 2 mM DTT). Proteins were eluted using 7 mL of elution buffer (Buffer B: Buffer C, 20:80, supplemented with 2 mM DTT). Eluted proteins were dialyzed at 4° C. using a 3,500 kDa MWCO (Thermo Fisher Scientific) cellulose membrane against Buffer A overnight and after a buffer change for 6 additional hours. Dialyzed proteins were then concentrated by reducing the volume 20-fold using an Amicon Ultra-4 Centrifugal Filter Unit with a 3,000 kDa MWCO (Millipore Sigma). The resulting co-purified proteins were aliquoted and stored at −80° C. Protein concentrations of the co-purified proteins were quantified using the Pierce 660 nm Protein Assay (ThermoFisher Scientific).

M7 Mass Spectrometry. The following protocol was used for peptide sample preparation: The proteins in the whole-cell extract preparations were quantified using BCA assay (Thermo Scientific). A volume equal to 150 µg of protein was used for S-Trap (PROTIFI) digestion. Digestion followed the S-trap protocol; briefly, the proteins were reduced and alkylated, the buffer concentrations were adjusted to a final concentration of 5% SDS 50 mM TEAB, 12% phosphoric acid was added at a 1:10 ratio with a final concentration of 1.2% and S-trap buffer (100 mM TEAB in 90% MeOH) is added at a 1:7 ratio (V/V ratio). The protein lysate S-trap buffer mixture was then spun through the S-trap column and washed 3 times with S-Trap buffer. Finally, 50 mM TEAB with 6 µg of trypsin (1:25 ratio) is added and the sample is incubated overnight with one addition of 50 mM TEAB with trypsin after two hours. The following day the digested peptides were released from the S-trap solid support by spinning at 3,000 g for 1 min with a series of solutions starting with 50 mM TEAB which is placed on top of the digestion solution, then 5% Formic acid followed by 50% Acetonitrile with 0.1% Formic Acid. The solution is then vacuum centrifuged to almost dryness and resuspended in 2% Acetonitrile 0.1% TFA (Triflouroacetic acid) and subjected to Fluorescent peptide quantification (Thermo Scientific).

The following protocol was used for peptide labelling with Tandem Mass Tags and fractionation: Two sets of TMT-10plex labels were used to label the sample. The replicates of each extract were split evenly across the two sets and the tags were assigned such that each replicate had a different mass tag to avoid unintentional bias. 20 µg of each sample was diluted with 50 mM TEAB to 25 µL per replicate. Two additional samples consisting of 5 µg of protein from each sample included in each TMT-10plex were pooled together to create a reference to account for bias between the two TMT runs. Each sample was labeled with TMT-10Plex Mass Tag Labeling Kit (Thermo Scientific). Briefly, 20 µL of each TMT label (126-131) was added to each digested peptide sample and incubated for an hour. The reaction was quenched with 1 µl of 5% Hydroxylamine and incubated for 15 minutes. All labeled samples were then mixed and lyophilized to almost dryness. The TMT labeled sample was reconstituted, desalted, and separated into 8 fractions by High pH fractionation (Thermo Scientific). One-third of each fraction (approximately 800 ng) was loaded on to the LC-MS/MS for analysis.

The following protocol was used for liquid chromatography and mass spectrometry of the samples: Liquid chromatography separation was conducted on a Dionex nano Ultimate 3000 (Thermo Scientific) with a Thermo Easy-Spray source. The digested peptides were reconstituted in 2% acetonitrile/0.1% trifluoroacetic acid and 1 µg in 5 µL of each sample was loaded onto a PepMap 100 Å 3 U 75 µm×20 mm reverse-phase trap where they were desalted online before being separated on a 100 Å 2 U 50 µm×150 mm PepMap EasySpray reverse-phase column. Peptides were eluted using a 120-minute gradient of 0.1% formic acid (A) and 80% acetonitrile (B) with a flow rate of 200 nL/min. The separation gradient was run with 2% to 5% B over 1 minute, 5% to 50% B over 89 minutes, 50% to 99% B over 2 minutes, a 4-minute hold at 99% B, and finally 99% B to 2% B held at 2% B for 18 minutes.

The following protocol was used for mass spectra acquisition: Mass spectra were collected on a Fusion Lumos mass spectrometer (Thermo Fisher Scientific) in a data-dependent MS3 synchronous precursor selection (SPS) method. MS1 spectra were acquired in the Orbitrap, 120K resolution, 50 ms max injection time, 5×105 max injection time. MS2 spectra were acquired in the linear ion trap with a 0.7 Da isolation window, CID fragmentation energy of 35%, turbo scan speed, 50 ms max injection time, 1×104 AGC, and maximum parallelizable time turned on. MS2 ions were isolated in the ion trap and fragmented with an HCD energy of 65%. MS3 spectra were acquired in the orbitrap with a resolution of 50K and a scan range of 100-500 Da, 105 ms max injection time, and 1×105 AGC.

The following process was followed for peptide and protein identification: Identification of peptides and proteins was conducted using the PAW pipeline [Wilmarth, P. A., Riviere, M. A. & David, L. L., *J. Ocul. Biol. Dis. Infor.* 2, 223-234 (2009)]. In brief, the ProteoWizard toolkit is used to convert the MS scans into intensity values and extract the TMT reporter ion peak heights. The Comet database search engine is then used to identify peptides. The *E. coli* BL21 (DE3) proteome UP000002032 and a list of known contaminants and expressed protein sequences were used for protein identification. Results are filtered based on a desired false discovery rate using the target decoy method. Identified proteins with sequence coverage of less than 5% were excluded from the downstream analysis.

The following process was used to scale the two TMT results: The protein intensities from the pooled samples in each 10plex were used to calculate scaling factors that can be applied to the intensity values from each sample in each TMT-10plex, eliminating the bias that results from independent MS runs[46].

The following process was used for the assignment of gene ontological function: Identified proteins were assigned gene ontological functions based on the gene ontology identifiers provided in the *E. coli* BL21 (DE3) proteome UP000002032. The gene ontology identifiers were grouped based on the general functional categories of interest.

M8 Protein quantification and SDS-PAGE analysis. Analysis of proteins by SDS-Polyacrylamide Gel Electrophoresis (PAGE) was carried out by separating proteins from whole-cell lysates and CFPS reactions using 4-20% Mini-PROTEAN TGX precast gels (Bio-Rad). We used Precision Plus Protein Dual Color Standards (10-250 kDa) as a reference standard for molecular weight verification. Protein gels were endpoint stained using PageBlue Protein Staining Solution (ThermoFisher Scientific) according to the manufacturer instructions. Gels were imaged using a PXi Imaging system (Syngene) and band analysis and protein quantification were carried out using the open-source platform for biological imaging analysis Fiji (http://fiji.sc/cgi-bin/gitweb.cgi/) and the proprietary software GeneTools (Syngene).

M9 Transmission Electron Microscopy. The following protocol was used for the assembly of the ferritin nanocage: 1 mL of FNA Buffer (25 mM HEPES, 50 mM NaCl, pH 7.5) was added to the cell-free reaction after expression of ferritin and then heat-treated at 90° C. for 10 mins. Ferrous sulphate heptahydrate was added drop by drop to a final concentration of 2.4 mM. The sample is then incubated overnight at 4° C. DLS and TEM analyses were performed to confirm the cage assembly.

The following protocol was used for TEM sample preparation: Samples were adsorbed on to the carbon-coated electron microscopy grid (Formvar carbon film on 300 mesh copper grids, Electron Microscopy Science) and dried at room temperature for 5 minutes. For samples with negative staining, the grid was placed on a droplet of 1.5% uranyl acetate for 3 minutes and the excess stain was removed with a soft wipe. The grid was air-dried for 5 minutes. All grids were stored in a drying cabinet until further use. The images were obtained in a transmission electron microscope (JEOL JEM-1400) operating at 100 kV.

M10 Statistical Analysis of results. Unless other is specified, statistical tests were performed using a standard two-tailed t-test. The exact p-value for each statistical analysis is reported directly in the figures unless p<0.00001. The number of replicates contributing to the calculation is listed in the figure legends. All error bars and measures of central tendency are defined in the figure legends.

Supplementary Note 1. Analysis of Protein Expression Through deGFP Quantification To measure the protein expression of our multi-strain cell lysates and controls, we designed a vector with the gene encoding deGFP under the control of the T7 promoter. Different versions of this plasmid were built and tested to find the vector that yielded the highest deGFP expression in our system (Methods, Section M1). For the quantification of deGFP produced by our *E. coli* cell-lysates, we constructed a calibration curve using purified eGFP (BioVision, Inc) as a standard (Methods, Section M4).

Supplementary Note 2. Optimization of Cell Lysate Preparation and Reaction Buffer The whole-cell lysate preparation protocol was optimized by varying pellet to sonication buffer ratio, energy input for the sonication of the cellular pellet, and runoff duration. Different growth media were tested following the same whole-cell lysate preparation protocol, and the media that showed an advantage over the others was incorporated into the protocol in all subsequent whole cell lysate preparations. The conditions for CFPS were optimized by varying template DNA concentration, expression time, temperature, and agitation speed during incubation. The optimized protocol for obtaining our multi-strain cell lysates and for the assembly of the CFPS reactions is detailed in Methods, Section M2.

The optimized reaction buffer used in this study is a modification of the S12 supplement described in our previous work[1]. Briefly, the S12 supplement used as an starting point for our optimized reaction buffer consists of the following: 50 mM HEPES (pH 7.6), 1.2 mM rATP, 0.8 mM rGTP/rCTP/rUTP, 0.17 mg mL$^{-1}$ tRNA, 34 μg mL$^{-1}$ Folinic acid, 12 mM Magnesium acetate, 50 mM Potassium gluconate, 80 mM Ammonium acetate, 2% PEG 8,000, 2 mM DTT, 4 mM Spermidine, 80 μg mL$^{-1}$ Creatine kinase, 67 mM Creatine phosphate, 0.64 mM cAMP, 1.5 mM of each 20 amino acids. The use of our optimized reaction buffer (Methods, Section M3.) resulted in ~2-fold more deGFP expressed compared to the S12 supplement control.

Supplementary Note 3. SDS-PAGE Analysis of CFPS Reactions Supplemented with Purified Translation Machinery To confirm that the translation machinery protein concentrations supplemented are comparable to those present in BL-18S$_{WCE}$ and BL-7S$_{WCE}$, we analyzed and compared the reactions in FIGS. 2B&C with control reactions through SDS-PAGE. The change in band intensities shows the staged increase in translation machinery proteins in the reactions supplemented with the purified mixtures. During gel analysis, it is noticeable that we can closely match and surpass the concentrations of the overexpressed proteins in BL-18S$_{WCE}$ and BL-7S$_{WCE}$.

Supplementary Note 4. Proteomics Analysis of Cell Lysates

To allow for quantitative comparisons of the proteins between the individual samples used for TMT-mass spectrometry, we also labelled and processed pooled samples comprised of equal portions of each extract to allow for internal reference scaling (IRS) normalization (Methods, Section M7). The principal component analysis of all replicates of each extract is shown in FIG. 3B. There is clear clustering of the replicates, indicating that they are representative without outliers.

There is a prominent difference between the intensities of the intentionally overexpressed proteins across the samples, as seen in FIG. 3C indicated in black. The intended enrichment of CFP and EF-Tu/EF-Ts is clearly observed in the BL-CFP$_{WCE}$ and BL-S1$_{WCE}$, respectively. All over-expressed proteins in BL-7S$_{WCE}$ were enriched by more than 2-fold with some as high as 12-fold, except for RF-1 and RF-2, which showed no significant difference. This result was anticipated because the strain expressing those proteins comprise ~1% of the total inoculum. There is also an 82% and 67% increase in the intensity of EF-Tu and EF-Ts, respectively, when comparing BL-S1$_{WCE}$ to BL-7S$_{WCE}$, as would be expected by the dilution of Strain-1 in BL-7S$_{WCE}$.

Met-tRNA transferase;
Ile-tRNA transferase;
Thr-tRNA transferase;
Lys-tRNA transferase;
Glu-tRNA transferase,
Asp-tRNA transferase;
Asn-tRNA transferase;
Leu-tRNA transferase;
Arg-tRNA transferase;
Cys-tRNA transferase;
Trp-tRNA transferase;
Phe-tRNA transferase B;
Pro-tRNA transferase;
Ser-tRNA transferase;
Phe-tRNA transferase A;
Gln-tRNA transferase;
Tyr-tRNA transferase;

SUPPLEMENTARY TABLE 1

Detailed strain composition of the 18-, 7- and 8-strain bacterium consortia.

| Strain | Gene 1 pIURAH backbone | Gene 2 pIURKL backbone | BL-18S | BL-7S | BL-8S |
|---|---|---|---|---|---|
| | | | | Relative density % | |
| 1 | EF-Tu | EF-Ts | 55.49 | 57.80 | 46.24-28.90 |
| 2 | IF1 | IF2 | 15.95 | 16.61 | 13.29-8.31 |
| 3 | EF-G | IF3 | 3.60 | 3.75 | 3.00-1.88 |
| 4 | Ala-tRNA transferase | EF4 | 7.97 | 8.30 | 6.64-4.15 |
| 5 | RF1 | RF2 | 0.48 | 0.50 | 0.40-0.25 |
| 6 | RF3 | RRF | 4.91 | 5.12 | 4.10-2.56 |
| 7 | EF-G | — | 7.59 | 7.91 | 6.33-3.96 |
| 8 | Leu-tRNA transferase | Met-tRNA formyltransferase | 0.63 | — | — |
| 9 | His-tRNA transferase | Glu-tRNA transferase | 0.57 | — | — |
| 10 | Phe-tRNA transferase A | Lys-tRNA transferase | 0.44 | — | — |
| 11 | Pro-tRNA transferase | Val-tRNA transferase | 0.37 | — | — |
| 12 | Met-tRNA transferase | Asp-tRNA transferase | 0.52 | — | — |
| 13 | Ile-tRNA transferase | Gln-tRNA transferase | 0.48 | — | — |
| 14 | Phe-tRNA transferase B | Trp-tRNA transferase | 0.45 | — | — |
| 15 | Asn-tRNA transferase | Ser-tRNA transferase | 0.35 | — | — |
| 16 | Tyr-tRNA transferase | Arg-tRNA transferase | 0.09 | — | — |
| 17 | Gly-tRNA transferase A | Cys-tRNA transferase | 0.07 | — | — |
| 18 | Gly-tRNA transferase B | Thr-tRNA transferase | 0.03 | — | — |
| 19 | Gam | — | — | — | 20-50 |

It is understood that the examples and embodiments described herein are for illustrative purposes only and that various modifications or changes in light thereof will be suggested to persons skilled in the art and are to be included within the spirit and purview of this application and scope of the appended claims. All publications, patents, and patent applications cited herein are hereby incorporated by reference in their entirety for all purposes.

What is claimed is:

1. A cell-free cell lysate from a cell mixture that heterologously expresses all of the following polypeptides:
   translational initiation factor 1 (IF1);
   translational initiation factor 2 (IF2);
   translational initiation factor 3 (IF3);
   translational elongation factor G (EF-G);
   translational elongation factor Tu (EF-Tu);
   translational elongation factor Ts (EF-Ts);
   translational elongation factor 4 (EF4);
   translational release factor 1 (RF1),
   translational release factor 2 (RF2),
   translational release factor 3 (RF3); and
   ribosome recycling factor (RRF).

2. The cell-free cell lysate of claim 1, wherein the polypeptides further comprise one or more or all of:
   Ala-tRNA transferase;
   Val-tRNA transferase;
   Met-tRNA formyltransferase;
   Gly-tRNA transferase B;
   His-tRNA transferase; and
   Gly-tRNA transferase A.

3. The cell-free cell lysate of claim 1, wherein the cell mixture comprises a plurality of different cells, wherein different cells heterologously express one or more of the polypeptides such that the cell mixture expresses each of the polypeptides.

4. The cell-free cell lysate of claim 1, wherein the cell mixture comprises seven different cells, wherein each of the seven different cells heterologously expresses different of one or more of the polypeptides.

5. The cell-free cell lysate of claim 1, wherein the cell mixture comprises the following cells:
   a first cell heterologously expressing EF-Tu and EF-Ts;
   a second cell heterologously expressing IF1 and IF2;
   a third cell heterologously expressing EF-G and IF3;
   a fourth cell heterologously expressing Ala-tRNA transferase and EF4;
   a fifth cell heterologously expressing RF1 and RF2;
   a sixth cell heterologously expressing RF3 and RRF;
   a seventh cell heterologously expressing EF-G.

6. The cell-free cell lysate of claim 1, wherein the cell lysate further comprises an exogenous nuclease inhibitor.

7. The cell-free cell lysate of claim 6, wherein the exogenous nuclease inhibitor is Gam.

8. The cell-free cell lysate of claim 6, wherein the nuclease inhibitor is expressed from a cell in the cell mixture.

9. The cell-free cell lysate of claim 1, wherein expression of one or more of polypeptides is encoded by a polynucleotide operably linked to an exogenous promoter.

10. The cell-free cell lysate of claim 9, wherein the exogenous promoter is a T7 promoter.

11. A method of performing cell-free protein translation, the method comprising,
   contacting an RNA comprising a protein coding sequence to the cell lysate of claim 1; and
   incubating the cell lysate under conditions to allow for translation of the protein coding sequence into a translated protein.

12. The method of claim 11, further comprising purifying the translated protein from the cell lysate.

* * * * *